(12) United States Patent
Nyberg et al.

(10) Patent No.: US 9,636,061 B2
(45) Date of Patent: *May 2, 2017

(54) SYSTEM AND METHOD FOR MEASURING BIOLOGICAL FLUID BIOMARKERS

(71) Applicant: CoreSyte, Inc., Great Falls, VA (US)

(72) Inventors: Sten Adam Nyberg, Dayton, OH (US); Dalton Pont, Sterling, VA (US)

(73) Assignee: CoreSyte, Inc., Great Falls, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/014,526

(22) Filed: Feb. 3, 2016

(65) Prior Publication Data

US 2016/0262666 A1    Sep. 15, 2016

Related U.S. Application Data

(60) Provisional application No. 62/130,039, filed on Mar. 9, 2015.

(51) Int. Cl.
| | |
|---|---|
| *A61B 5/05* | (2006.01) |
| *A61B 5/1477* | (2006.01) |
| *A61B 5/145* | (2006.01) |
| *A61B 5/00* | (2006.01) |
| *A61B 10/00* | (2006.01) |

(52) U.S. Cl.
CPC .......... *A61B 5/1477* (2013.01); *A61B 5/0024* (2013.01); *A61B 5/14517* (2013.01); *A61B 5/4266* (2013.01); *A61B 5/6833* (2013.01); *A61B 10/0064* (2013.01); *A61B 5/0017* (2013.01); *A61B 5/14546* (2013.01); *A61B 2562/164* (2013.01)

(58) Field of Classification Search
CPC ............ A61B 10/0064; A61B 10/0096; A61B 5/14517; B01L 2300/023; B01L 2300/0645; B01L 2300/0803; B01L 2400/0406; G01N 27/3273; G01N 27/3271; G01N 27/3272
See application file for complete search history.

(56) References Cited

U.S. PATENT DOCUMENTS

| | | | |
|---|---|---|---|
| 5,310,469 | A | 5/1994 | Cunningham et al. |
| 5,718,816 | A | 2/1998 | Savage et al. |

(Continued)

FOREIGN PATENT DOCUMENTS

| | | | |
|---|---|---|---|
| WO | 8700286 A1 | | 1/1987 |
| WO | WO2010045247 | * | 4/2010 |

(Continued)

OTHER PUBLICATIONS

Liu, et al. "Implementation of a microfluidic conductivity sensor—A potential sweat electrolyte sensing system for dehydration detection," in Conf Proc IEEE Eng Med Biol Soc, 2014:1678-81, 5 pgs.

(Continued)

*Primary Examiner* — Navin Natnithithadha
*Assistant Examiner* — Eric Messersmith
(74) *Attorney, Agent, or Firm* — NEO IP

(57) ABSTRACT

Systems and methods of analyzing biological fluid biomarkers, calculating biomarker data, transmitting data to a transceiver device, and storing the data and/or analytics in a database and/or on at least one remote computer server.

20 Claims, 42 Drawing Sheets

(56) References Cited

U.S. PATENT DOCUMENTS

| | | | |
|---|---|---|---|
| 6,198,953 | B1 | 3/2001 | Webster et al. |
| 7,575,549 | B2 | 8/2009 | Miller |
| 8,388,534 | B2 | 3/2013 | Jang et al. |
| 2003/0163287 | A1 | 8/2003 | Vock et al. |
| 2006/0253011 | A1 | 11/2006 | Edmonson et al. |
| 2007/0096604 | A1 | 5/2007 | Edmonson et al. |
| 2007/0179371 | A1 | 8/2007 | Peyser et al. |
| 2008/0039700 | A1 | 2/2008 | Drinan et al. |
| 2010/0176006 | A1 | 7/2010 | Bickford et al. |
| 2013/0245388 | A1 † | 9/2013 | Rafferty |
| 2014/0330096 | A1 | 11/2014 | Brunswick |
| 2014/0350432 | A1 | 11/2014 | Khalfallah et al. |
| 2015/0019135 | A1 | 1/2015 | Kacyvenski et al. |
| 2015/0057515 | A1* | 2/2015 | Hagen ............. A61B 10/0064 600/346 |
| 2015/0112164 | A1 | 4/2015 | Heikenfeld et al. |
| 2015/0112165 | A1 | 4/2015 | Heikenfeld |

FOREIGN PATENT DOCUMENTS

| | | |
|---|---|---|
| WO | 2013152087 A2 | 10/2013 |
| WO | 2014197822 A2 | 12/2014 |
| WO | 2015058055 A1 | 4/2015 |
| WO | 2015058064 A1 | 4/2015 |
| WO | 2015184084 | 12/2015 |
| WO | 2015184097 A2 | 12/2015 |
| WO | 2016007944 A2 | 1/2016 |
| WO | 2016049019 A1 | 3/2016 |
| WO | 2016061362 A2 † | 4/2016 |
| WO | 2016130905 A1 | 8/2016 |
| WO | 2016134235 A1 | 8/2016 |
| WO | 2016138087 A1 | 9/2016 |

OTHER PUBLICATIONS

Jason Heikenfeld, "Let Them See You Sweat", IEEE Spectrum, Nov. 2014, p. 46.

Daniel P. Rose, M. Ratterman, Daniel K. Griffin, Linlin Hou, Nancy Kelley-Loughnane, Rajesh R. Naik, Joshua A. Hagen, I. Papautsky, Jason Heikenfeld, Adhesive RFID Sensor Patch for Monitoring of Sweat Electrolytes, IEEE Transactions on Biomedical Engineering, Paper ID # TBME-00773-2014-R1, Manuscript received Jun. 18, 2014; revised Sep. 10, 2014; accepted Nov. 6, 2014.

Jason C. Heikenfeld, U.S. Appl. No. 62/023,233, Provisional Patent Application; Entire Document.

University of Cincinnati, U.S. Appl. No. 62/003,675, Provisional Patent Application; Entire Document.

University of Cincinnati, U.S. Appl. No. 62/003,707, Provisional Patent Application; Entire Document.

University of Cincinnati, U.S. Appl. No. 61/620,069, Provisional Patent Application; Entire Document.

Jason C. Heikenfeld, U.S. Appl. No. 61/892,859, Provisional Patent Application; Entire Document.

Jason C. Heikenfeld, Advanced Adhesives for Chronological Sweat Sensors, U.S. Appl. No. 62/074,295, Provisional Patent Application filed Nov. 3, 2014; Specification including the claims, abstract, and drawings.

Rose, Adhesive RFID Sensor Patch for Monitoring of Sweat Electrolytes, 9, Nov. 6, 2014, IEEE Transactions on Biomedical Engineering.†

Rose et al., Adhesive RFID Sensor Patch for Monitoring of Sweat Electrolytes, 9 pages, Nov. 6, 2014, IEEE Transactions on Biomedical Engineering.†

* cited by examiner
† cited by third party

PRIOR ART FIG. 1

| | Symptoms | Degraded Performance | Injury |
|---|---|---|---|
| Low Electrolytes | Cramps, Headaches | Slower, Lock Up | Tissue /Tendon Tear |
| Metabolite Imbalance | Nausea, Vomit, Disorient | Cognitive Errors | TBI, Neural Damage |
| Small Molecule Build Up | Stiffness, Fatigue | Shut Down | Organ Damage |
| Signal Protein Presence | Fever, Fatigue | Incapacitated | Organ Failure |

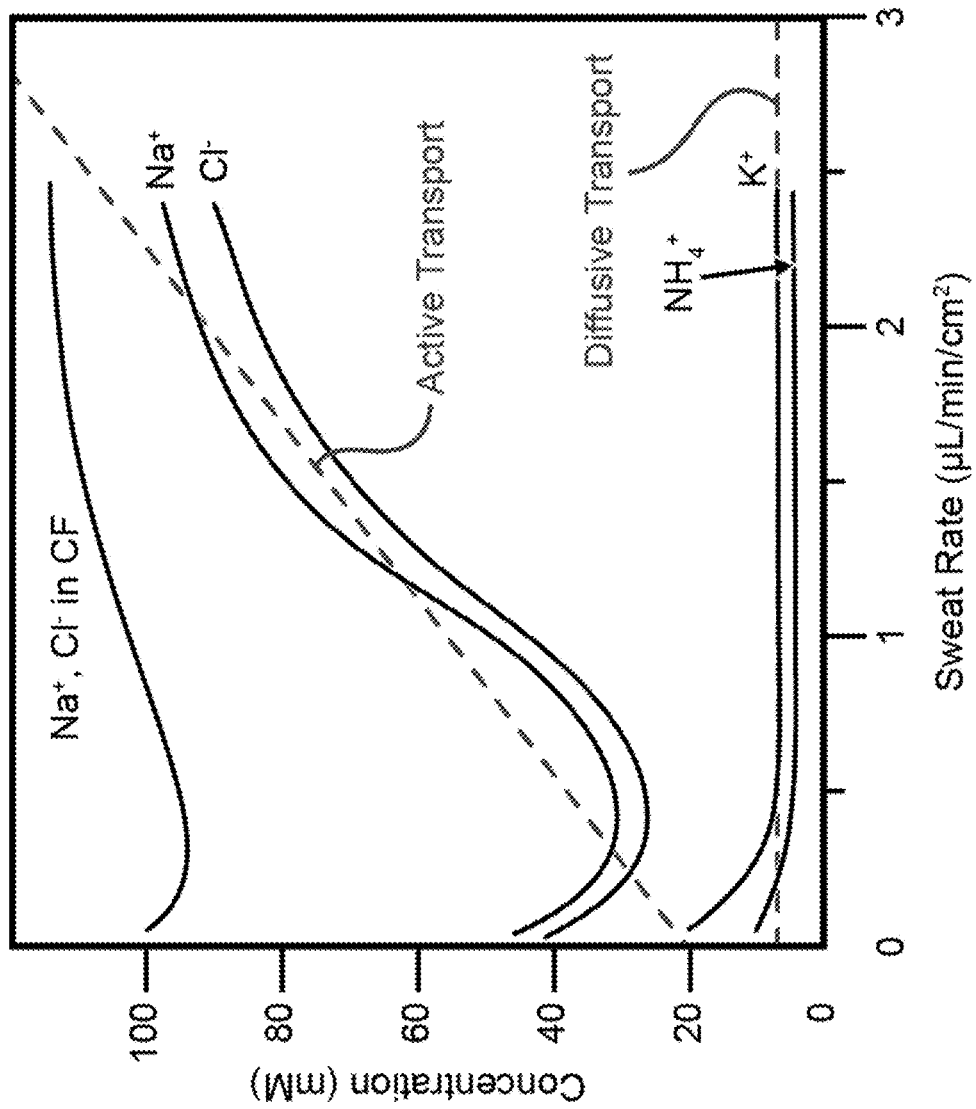
PRIOR ART FIG. 2

FIG. 3
| ITEM NO. | PART NUMBER | DESCRIPTION | QTY. |
|---|---|---|---|
| 1 | 3M 9917 | Double Sided Adhesive | 1 |
| 2 | 3M 9926T | Woven Top Adhesive | 1 |
| 3 | Key Electronics PCB | Polyimide Flex PCB | 1 |
| 4 | GE Whatman 1001 | Grade 1 Filter Paper | 1 |
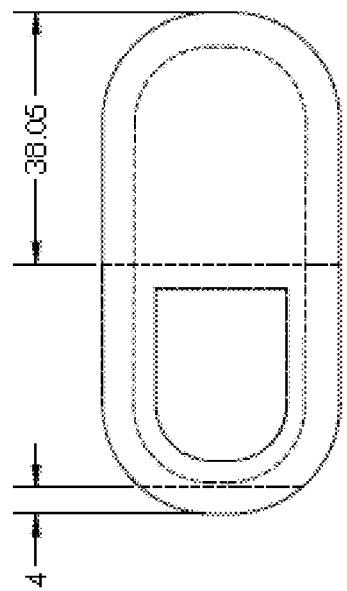
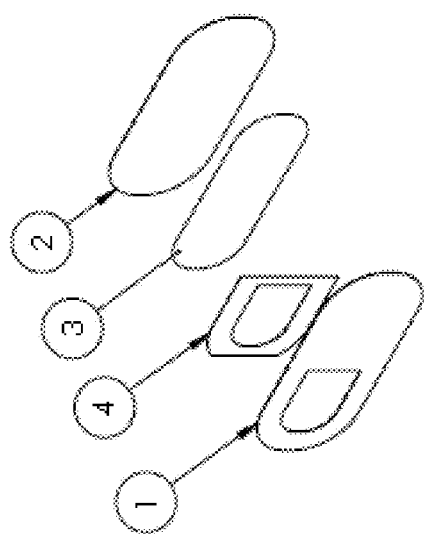

Basic Ratio for Sweat Flow Rate (SFR)

| K (mV : mM) | Na (mV : mM) | Ratio (Na/K) | SFR (uL/min/cm$^2$) |
|---|---|---|---|
| 25 : 5 | 100 : 20 | 4 | 0.0 |
| 25 : 5 | 150 : 30 | 6 | 0.5 |
| 25 : 5 | 250 : 50 | 10 | 1.0 |
| 25 : 5 | 400 : 80 | 16 | 1.5 |
| 25 : 5 | 450 : 90 | 18 | 2.0 |
| 25 : 5 | 500 : 100 | 20 | 2.5 |
| 25 : 5 | 550 : 110 | 22 | 3.0 |

Body Surface Area (BSA) Calcs

| | |
|---|---|
| DuBois and DuBois[1] | BSA (m2) = 0.007184 x Height(cm)0.725 x Weight(kg)0.425 |
| Gehan and George[2] | BSA (m2) = 0.0235 x Height(cm)0.42246 x Weight(kg)0.51456 |
| Haycock[3] | BSA (m2) = 0.024265 x Height(cm)0.3964 x Weight(kg)0.5378 |
| Mosteller[4] (CoreSyte Uses) | BSA (m2) = SQR RT ( [Height(cm) x Weight(kg)] / 3600 ) |

Sweat Loss & Body Mass Loss Calcs

| | | | |
|---|---|---|---|
| Sweat Loss 1 | SFR1 x (Use Ratio) | BSA x (Use Calc) (User Ht Wt Inputs) | Dur (From Session Time) |
| Sweat Loss 2 | SFR2 x (KSI table, User Wt Input, Phone Temp) (Sweat Stds Table) | | Dur (Sess Time) |
| Sweat Mass | Convert SL1 Vol (L) to Mass (Kg) | | |
| % Body Mass Loss | Sweat Mass/User Wt | | |
| Sweat Loss Ratio (SLR) | SL1/SL2 (Sweat More/Less Than Norm) | | |

FIG. 11A

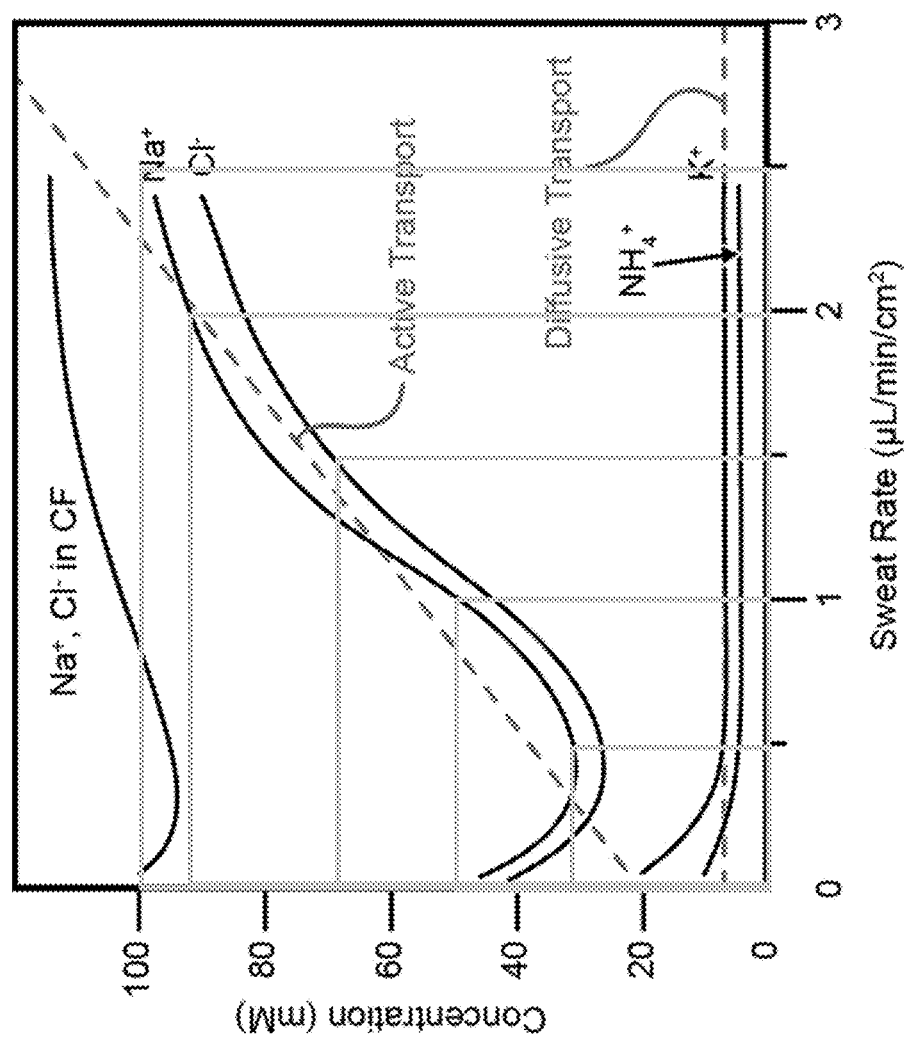
PRIOR ART FIG. 11B

FIG. 11D

Sweat Stds for Typical User (KSI, ACSM, GSSI, Runners World)

| BSA | Temp (°F) | Sweat (oz/min) | SFR2 | |
|---|---|---|---|---|
| 100 lbs | 50 | 0.3 | 0.61045569 | Zone 1 |
| Ave Ht 60" | 60 | 0.3 | | |
| Ave BSA (m²) | 70 | 0.3 | | |
| 1.45335018 | 80 | 0.4 | | |
| | 90 | 0.4 | | |
| | 100 | 0.5 | 0.95638058 | Zone 2 |
| 120 lbs | 50 | 0.4 | | |
| Ave Ht 66" | 60 | 0.4 | | |
| Ave BSA (m²) | 70 | 0.4 | | |
| 1.65707416 | 80 | 0.4 | | |
| | 90 | 0.5 | | |
| | 100 | 0.6 | 0.99942278 | |
| 140 lbs | 50 | 0.4 | | |
| Ave Ht 70" | 60 | 0.4 | | |
| Ave BSA (m²) | 70 | 0.5 | | |
| 1.833128673 | 80 | 0.5 | | |
| | 90 | 0.6 | | |
| | 100 | 0.7 | 1.04863311 | |
| 160 lbs | 50 | 0.5 | | |
| Ave Ht 73" | 60 | 0.5 | | |
| Ave BSA (m²) | 70 | 0.5 | | |
| 1.992893964 | 80 | 0.6 | | |
| | 90 | 0.7 | | |
| | 100 | 0.7 | 1.09812224 | |
| 180 lbs | 50 | 0.5 | | |
| Ave Ht 75" | 60 | 0.6 | | |
| Ave BSA (m²) | 70 | 0.6 | | |
| 2.135530278 | 80 | 0.7 | | |
| | 90 | 0.7 | | |
| | 100 | 0.8 | 1.16325978 | |
| 200 lbs | 50 | 0.6 | | |
| Ave Ht 76" | 60 | 0.6 | | |
| Ave BSA (m²) | 70 | 0.7 | | |
| 2.260032813 | 80 | 0.7 | | |
| | 90 | 0.8 | | |
| | 100 | 0.9 | 1.21696552 | |
| 220 lbs | 50 | 0.7 | | |
| Ave Ht 77" | 60 | 0.7 | | |
| Ave BSA (m²) | 70 | 0.7 | | |
| 2.38071595 | 80 | 0.8 | | |
| | 90 | 0.9 | | |
| | 100 | 1.0 | 1.26711883 | Zone 3 |
| 240 lbs | 50 | 0.7 | | |
| Ave Ht 77" | 60 | 0.8 | | |
| Ave BSA (m²) | 70 | 0.8 | | |
| 2.482067957 | 80 | 0.9 | | |
| | 90 | 1.0 | | |
| | 100 | 1.2 | 1.42995279 | |
| 260+ lbs | 50 | 0.8 | | |
| Ave Ht 77" | 60 | 0.8 | | |
| Ave BSA (m²) | 70 | 1.0 | | Zone 4 |
| 2.579440686 | 80 | 1.4 | | |
| | 90 | 1.8 | | |
| | 100 | 2.2 | 2.52287251 | |

Normal Sweat Rate Range

Elite Pro/NCAA Athletes Much Higher than Typical Users

FIG. 12A

| Basic Concentration Conversions | | | | | |
|---|---|---|---|---|---|
| K (mV) | K (mM) | Na (mV) | Na (mM) | | |
| 0 | 0 | 0 | 0 | Specified Range | |
| 17 | 40 | 57 | 110 | Specified Range | |
| 30 | 14 | 50 | 17 | Test Range | |
| 80 | 135 | 130 | 171 | Test Range | |
| K Ratio | 2.4 | Na Ratio | 1.9 | mM/mV | |

FIG. 12B

Ratiometric Analysis

| Trend 1 | Sweat Loss Ratio - User Sweat Loss vs Norm Sweat Loss | | | | | | |
|---|---|---|---|---|---|---|---|
| | SLR = | SL1/SL2 | > | 1 | Sweating Trend More Than Norm | | |
| | | | < | 1 | Sweating Trend Less Than Norm | | |

| Trend 2 | Electrolyte Trend Ratio - User 1st Time Derivative vs Norm Electrolyte Change | | | | | | |
|---|---|---|---|---|---|---|---|
| | $\frac{dNa\ (mV)}{dT}$ | X | SLR | X | Na Loss Norm | = | Na Trend (Approx Loss Given User Sensor Changes) |
| | $\frac{dK\ (mV)}{dT}$ | X | SLR | X | K Loss Norm | = | K Trend (Approx Loss Given User Sensor Changes) |
| | From Sensor | | From Above | | From UT/GSSI | | |

FIG. 12C

| Basic mV Ratios (Same as mM Ratios) | | | | |
|---|---|---|---|---|
| Na/K(mV) | SFR1 | | | |
| 1 | | | | |
| 2 | | | | |
| 3 | | | | |
| 4 | 0.00 | | | Zone 1 |
| 5 | 0.25 | | | Zone 1 |
| 6 | 0.50 | 0.125 | | Zone 1 |
| 7 | 0.63 | | | Zone 2 |
| 8 | 0.75 | | | Zone 2 |
| 9 | 0.88 | | | Zone 2 |
| 10 | 1.00 | 0.083 | | Zone 2 |
| 11 | 1.08 | | | Zone 3 |
| 12 | 1.17 | | | Zone 3 |
| 13 | 1.25 | | | Zone 3 |
| 14 | 1.33 | | | Zone 3 |
| 15 | 1.42 | | | Zone 3 |
| 16 | 1.50 | 0.250 | | Zone 3 |
| 17 | 1.75 | | | Zone 4 |
| 18 | 2.00 | | | Zone 4 |
| 19 | 2.25 | | | Zone 4 |
| 20 | 2.50 | | | Zone 4 |
| 21 | 2.75 | | | Zone 5 |
| 22 | 3.00 | | | Zone 5 |
| 23 | 3.25 | | | Zone 6 |
| 24 | 3.50 | | | Zone 6 |
| 25 | | | | Zone 6 |

FIG. 13A

| (Please See Level Calc for Na) | Level 1 | Level 2 | Level 3 | | HYDRATION | | | |
|---|---|---|---|---|---|---|---|---|
| | K | Na 1 | Na 2 | Na 3 | % Body Mass | SLR | Na Trend | K Trend |
| Range Low | 0 | 20 | 20 | 20 | 0 | 0 | 0 | TBD |
| Range High | 20 | 110 | 110 | 110 | 7 | 3 | | |
| Red Lo | <3 | <35 | <37 | <54 | <54 | <0.25 | | |
| Yellow Lo1 | 3 | 36 | 38 | 54 | | 0.25 | | |
| Yellow Lo2 | 3.9 | 37 | 39 | 56 | | 0.49 | | |
| Green Lo1 | 4 | 38 | 40 | 57 | | 0.50 | | |
| Green Lo2 | 4.9 | 42 | 44 | 63 | 0 | 0.99 | | |
| Blue Low | 5 | 43 | 45 | 65 | 1.00% | 1.00 | | |
| Blue High | 6 | 45 | 47 | 68 | 1.99% | 1.00 | | |
| Green Hi1 | 6.1 | 46 | 48 | 70 | 2.00% | 1.10 | | |
| Green Hi2 | 9 | 48 | 50 | 73 | 2.99% | 1.50 | | |
| Yellow Hi1 | 9.1 | 49 | 51 | 74 | 3.00% | 1.51 | | |
| Yellow Hi2 | 14 | 59 | 62 | 89 | 3.99% | 1.75 | | |
| Red Hi | >14 | >59 | >62 | >89 | 4% | >1.75 | | |
| | I1 Std | I2 Ratio | I3 Ratio | SL1 Derived | SL1/SL2 | | | |
| | 1.0000 | 0.04651163 | 0.44444444 | via Sensors | Compares | | | |
| | SFR <1 | SFR <2>1 | SFR >2 | | to Normal | | | |
| | | uL/min/cm² | | | | | | |
| | Only Showing 1 Na in Gauge | | | | | | | |

Color Thresholds

FIG. 13B

| Intense Selection | User Input at Session Start | | From Phone | From Sensor |
|---|---|---|---|---|
| | User Input | User Wt Input | Atm Temp | Na/K Ratio |
| User Input Low (1) | | wt<140 (1) | T°F<80 (1) | <10 (1) |
| User Input Med (2) | | wt<200>140 (2) | T°F<90>80 (2) | 10-18 (2) |
| User Input High (3) | | wt>200 (3) | T°F>90 (3) | >18 (3) |
| | | | Not Skin T | |
| These values should be adjustable in the CLOUD | | | | |

| | | |
|---|---|---|
| Level 1 | Add Up Scores from Inputs Above Intens+Wt+Temp+Ratio | <4 |
| Level 2 | | 4-10 |
| Level 3 | | >10 |

Multi-User View
(Active Session Chrono)

Selected User History
(Multi-Biomarker History Chrono)

FIG. 28
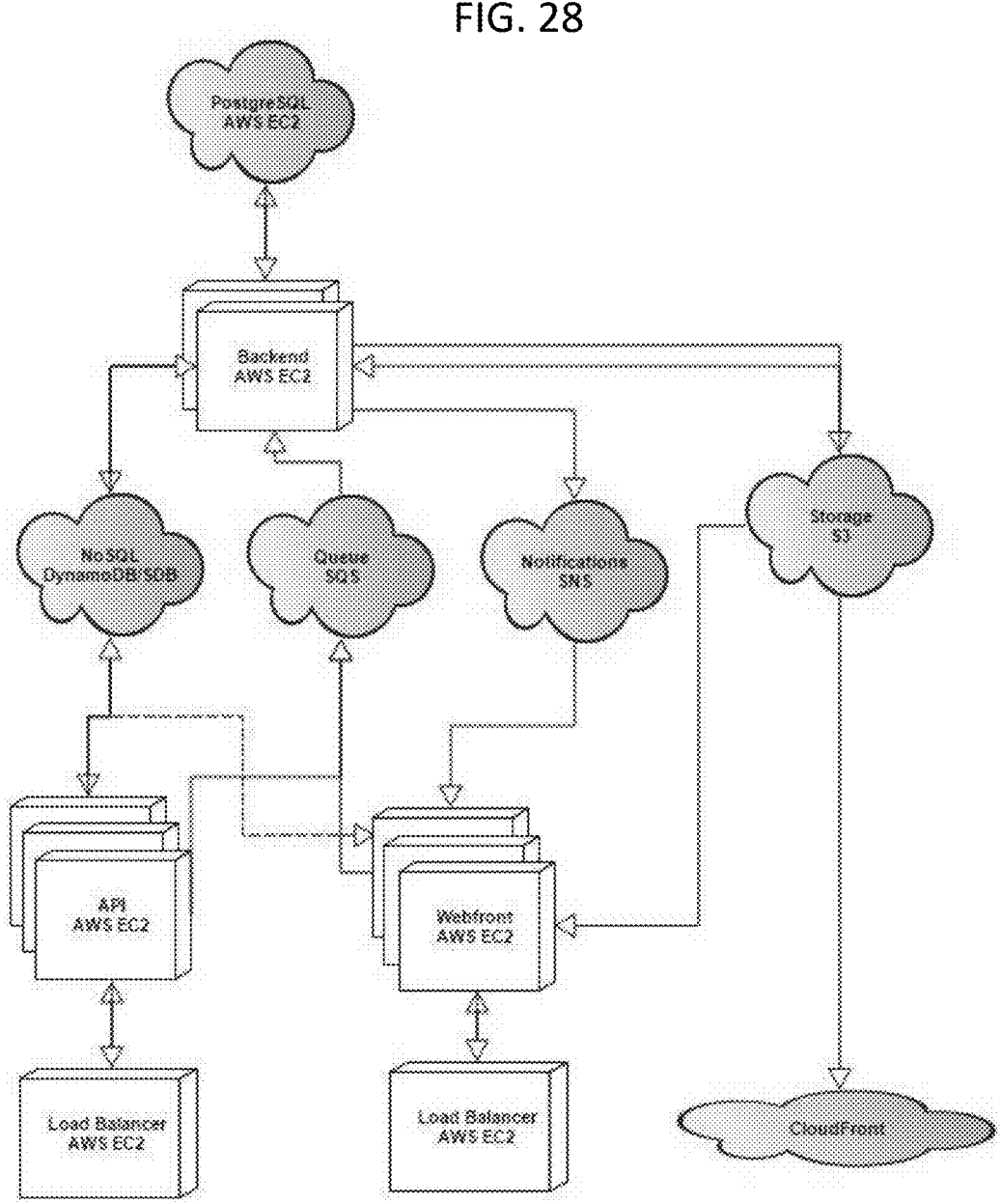
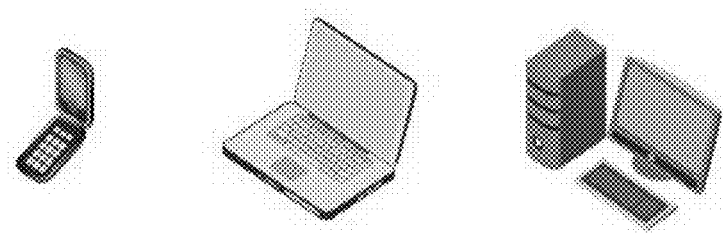

SYSTEM AND METHOD FOR MEASURING BIOLOGICAL FLUID BIOMARKERS

CROSS REFERENCE TO RELATED APPLICATIONS

This application claims priority from U.S. Provisional Patent Application No. 62/130,047, filed Mar. 9, 2015, which is incorporated herein by reference in its entirety.

BACKGROUND OF THE INVENTION

1. Field of the Invention

The present invention is generally directed to a system and method including a device for sensing and collecting biological fluid inputs and transmitting inputs to a remote computing device for analyzing the biological fluid inputs.

2. Description of the Prior Art

Generally, biomarkers from biological fluid have significant prognostic and/or diagnostic utility, such as predicting disease, nutritional imbalance, or psychological or physical stress; however, many of the most utilized biomarkers are collected from blood. The ability to predict events through non-invasive means, such as sweat detection, provides great utility to persons under physical stress, particularly individuals in the process of physical activity or exercise. The ability to monitor sweat biomarkers real time and continuously during activity allows an individual to make informed decisions regarding hydration, nutrition, and exertional status, and recovery all variables that moderate physical performance.

For example, hydration status is a predictor of physical performance; dehydration as low as 1% of body mass can impair performance. Prior art detection and treatment, as shown in FIG. 1, is currently at the stages of when symptoms present, performance degrades, and/or injury presents. Determining hydration through sweat biomarkers before dehydration symptoms present has many benefits, such as reducing fatigue, cramps, and headaches. Therefore, developing a device and system for non-invasively obtaining biomarkers, such as through sweat, is needed.

Sweat contains a multitude of biomarkers; any substance aqueously dissolvable in the blood can present in the sweat by way of eccrine glands. The sweat biomarkers can be small molecules, proteins, metabolites, and/or electrolytes. Well-known electrolytes in sweat are sodium and potassium. As shown in FIG. 2, potassium concentration is not dependent upon sweat rate due to the passive diffusive transport of potassium, while sodium and chloride concentrations in sweat are dependent upon sweat rate due to the active transport of sodium. Thus, monitoring sodium or chloride concentrations is an accurate, indirect means of indicating hydration status of an individual. Therefore, developing a sweat biomarker monitoring device that can communicate to an individual real-time biomarker data is needed.

U.S. Pat. No. 6,198,953 for method and system for continuous sweat collection and analysis by Webster, et al. filed Mar. 11, 1999 and issued Mar. 6, 2001 is directed to a method and system of the invention provide especially for continuously obtaining and analyzing, on a real time basis, sweat from a selected area of skin on the body of a person, especially a neonate, being diagnosed for cystic fibrosis, by causing sweating of the selected area of skin, by placing an electrically positive iontophoretic electrode device of a set of said devices over the selected area of skin preferably within a previously placed receiving and holding device which, following the induction of sweat and removal of the electrically positive iontophoretic electrode device, receives a sweat-sensing electrode device that continuously sends electrical signals to sweat analysis circuitry for providing a digital readout of the ionic composition of the sweat.

U.S. Pat. No. 8,388,534 for an apparatus providing skin care information by measuring skin moisture content by Jang, et al. filed Sep. 24, 2007 and issued Mar. 5, 2013 is directed to an apparatus for providing skin care information, the apparatus including: an electrode unit supplying a voltage to a user's skin and detecting a current signal in the user's skin; a measurement control unit measuring the user's skin moisture content and sweat gland activity by using the detected current signal; a data calculation unit deriving skin moisture content information by using the skin moisture content and the sweat gland activity, and generating skin care information corresponding to the skin moisture content information; and an information provider providing the user with the generated skin care information is provided.

U.S. Pat. No. 7,575,549 for an apparatus and method for increasing, monitoring, measuring, and controlling perspiratory water and solid loss at reduced ambient pressure by Miller filed Jul. 30, 2004 and issued Aug. 18, 2009 is directed to a device for increasing, monitoring, and measuring perspiration water and solid loss at reduced ambient pressure, comprising a sealed chamber capable of maintaining less than atmospheric pressure for an extended period of time and a gasket-sealed door accessing the chamber. An algorithm allowing for continuous calculations of sweat loss and fluid replacement requirements of the occupant of the chamber is disclosed.

US patent application 2014/330,096 for performing a physiological analysis with increased reliability by Brunswick filed Nov. 12, 2012 and issued Nov. 6, 2014 is directed to a method for performing an electrophysiological analysis implemented in a system includes: a series of electrodes to be placed on different regions of the human body; a DC voltage source controlled so as to produce DC voltage pulses; a switching circuit for selectively connecting the active electrodes to the voltage source, the active electrodes forming an anode and a cathode, and for connecting at least one other high-impedance passive electrode used to measure the potential reached by the body; and a measuring circuit for reading data representative of the current in the active electrodes, and data representative of the potentials generated on at least certain high-impedance electrodes in response to the application of the pulses, the data allowing a value to be determined for the electrochemical conductance of the skin.

US patent application 2014/350,432 for assessment of relative proportions of adrenergic and cholinergic nervous receptors with non-invasive tests by Khalfallah and Brunswick filed Aug. 8, 2014 and issued Nov. 27, 2014 is directed to a system and method for assessing relative proportions of cholinergic and adrenergic nervous receptors in a patient is disclosed. The system includes: an anode, a cathode, and passive electrode for placement on different regions of the patient body. The method generally includes: applying DC voltage pulses of varying voltage values to stress sweat glands of the patient, collecting data representing the current between the anode and the cathode and the potential of the anode, the cathode, and the passive electrode for each of the different DC voltage, and computing data representing the electrochemical skin conductance of the patient. The computed data representing the electromechanical skin conductance of the patient is reconciled with reference data from control patients having known relative proportions of cholinergic and adrenergic nervous receptors. Thus, the relative proportions of cholinergic and adrenergic nervous receptors in the patient can be determined.

US patent application 2015/019,135 for motion sensor and analysis by Kacyvensky, et al. filed Jun. 3, 2014 and issued Jan. 15, 2015 is directed to the performance of an individual being monitored based on measurements of a conformal sensor device. An example system includes a communication module to receive data indicative of a measurement of at least one sensor component of the conformal sensor device. The sensor component obtains measurement of acceleration data representative of an acceleration proximate to the portion of the individual. A comparison of a parameter computed based on the sensor component measurement to a preset performance threshold value provides an indication of the performance of the individual.

Published article by Liu, et al. in Conf Proc IEEE Eng Med Biol Soc, 2014:1678-81, discusses the implementation of a microfluidic conductivity sensor—a potential sweat electrolyte sensing system for dehydration detection.

Although biomarkers in sweat are appreciated, specifically electrolytes and glucose, a system and method is still lacking that continuously analyzes sweat biomarkers in real time and transmits data to a user, which informs the user of his or her health status.

SUMMARY OF THE INVENTION

The present invention presents a system and method including a device for sensing and collecting biological fluid inputs and transmitting inputs via a wireless network to a remote computing device for analyzing the biological fluid inputs and fluid biomarkers, calculating biomarker data, and storing the data in a database and/or on the computing device and/or on a remote computer server.

The system includes an apparatus or device including at least one electrochemical sensor, a microcontroller, and a transceiver antenna coil; at least one remote transceiver device; and at least one remote computer server. The apparatus analyzes at least one biological fluid biomarker, calculates at least one output datum of the at least one biological fluid biomarker, and transmits the at least one output datum to the at least one remote transceiver device. The at least one remote transceiver device transmits the at least one datum with the at least one remote computer server or at least one remote computing device or database for storage. The apparatus and the at least one remote transceiver device have real-time or near-real-time two-way communication.

The method includes the steps of providing an apparatus including at least one electrochemical sensor, a microcontroller, and a transceiver antenna coil; at least one remote transceiver device; and at least one remote computer server. The at least one remote transceiver device and the apparatus being operable for two-way cross-communication in real-time or near-real-time. The electrochemical sensor sensing at least one biomarker, which creates a voltage. The microcontroller converting the at least one biomarker into at least one output datum using at least one algorithm. The at least one remote transceiver device inputting modifying variables into the at least one algorithm via the two-way communication with the apparatus. The transceiver antenna coil transmitting the at least one output datum to the at least one remote transceiver device via the two-way communication with the apparatus. The at least one remote transceiver device sharing or transmitting the at least one datum with the at least one remote computer server or device or database for storage.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 1 shows a chart demonstrating biomarker types, changes in biomarker levels during progressive stages of injury, and physiological presentations associated with each stage of injury.

FIG. 2 shows a chart relating sweat rate to concentration of electrolytes.

FIG. 3 shows the multiple layers and associated parts of the sensor apparatus and a top perspective view of the complete sensor apparatus.

FIG. 11A shows a table of various sweat characteristics including basic ratio for sweat flow rate, body surface area calcs, and sweat loss & body mass loss calcs.

FIG. 11B shows a chart of concentration of ions vs. sweat rate.

FIG. 11D shows a table of sweat stds for a typical user.

FIG. 12A shows a table of basic electrolyte concentration conversions.

FIG. 12B shows a table of ratiometric analysis used within the sensor apparatus.

FIG. 12C shows a table of basic mV ratios.

FIG. 13A shows thresholds for electrolyte concentrations.

FIG. 13B shows a table of user input at session start, input from phone, and input from sensor.

FIG. 28 shows a diagram of the generic cloud architecture.

DETAILED DESCRIPTION

The present invention provides systems and methods including a device for sensing and collecting biological fluid inputs and transmitting inputs to a remote computing device for analyzing the biological fluid inputs or analyzing biological fluid biomarkers, calculating biomarker data, and storing the data in a database and/or on the computing device and/or on a remote computer server.

Figure 4:
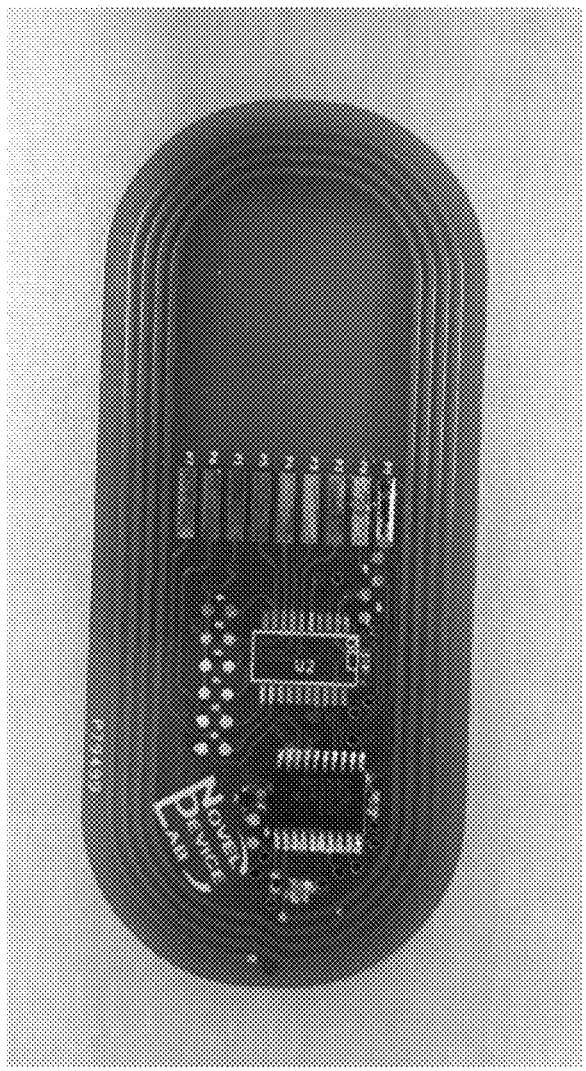
FIG. 4 shows a perspective top view of a flexible electronic layer on the bottom adhesive layer.
Figure 5:
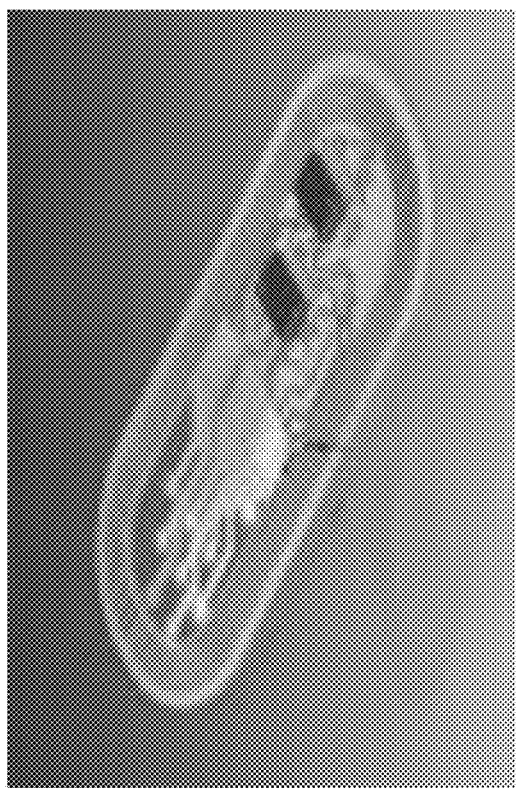
FIG. 5 shows a complete flexible electronic layer.
Figure 6:
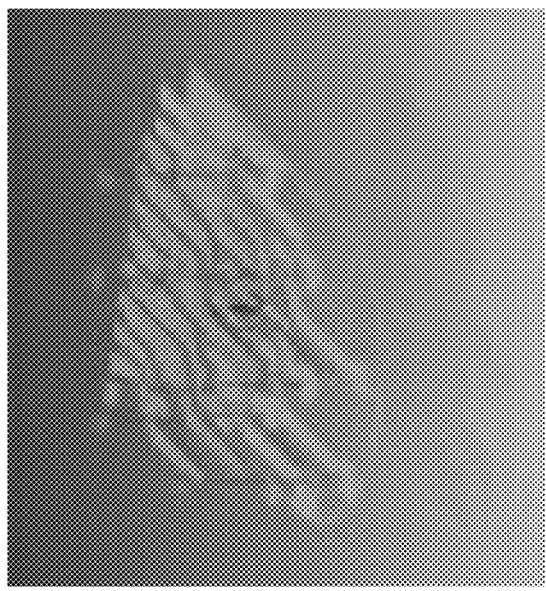
FIG. 6 shows a separated layer of electrochemical sensors.
Figure 8:
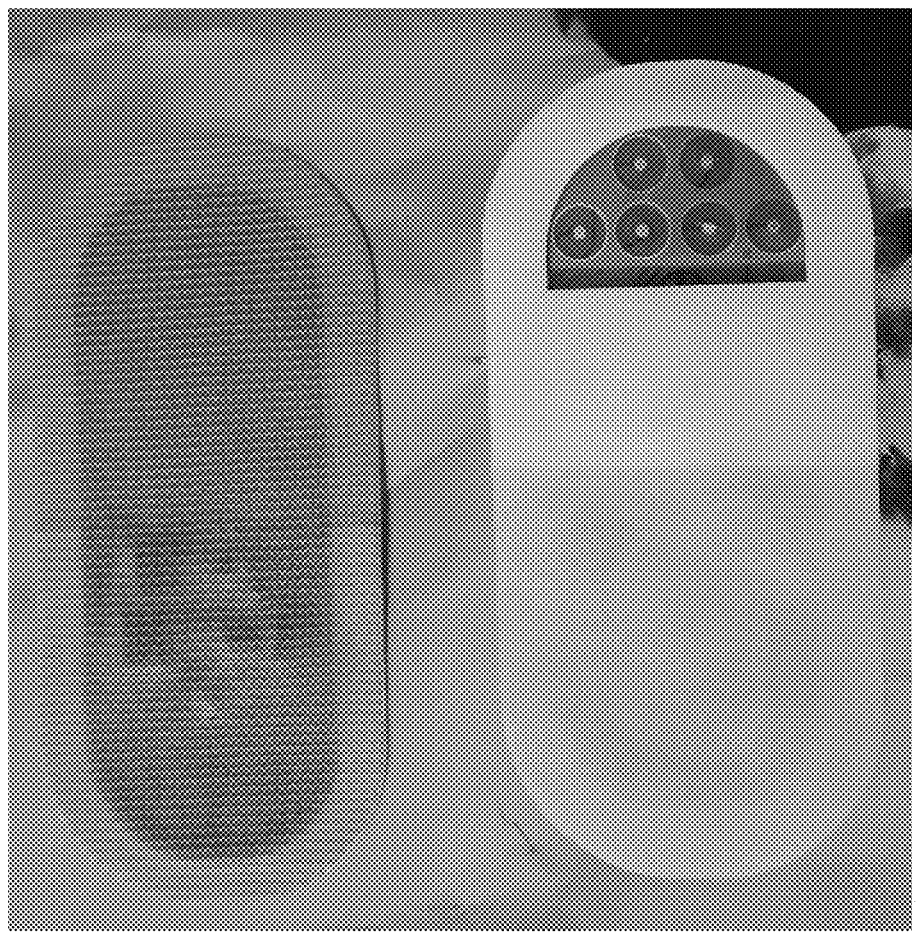
FIG. 8 shows a top perspective view (top) and bottom perspective (bottom) view of a complete sensor apparatus.

One component of the system is a sensor apparatus or device for sensing sweat biomarkers. FIG. 3 illustrates a multi-layered apparatus or device that includes a double-sided adhesive layer, a filter paper, an electronic layer, and a woven top adhesive. More specifically, the device is flexible and multi-layered, wherein the layers comprise the following: a macrofluidic, double-sided adhesive layer; an electronic layer comprising at least one electrochemical sensor, a microcontroller, and a transceiver antenna coil; a microfluidic management layer; and a vapor porous, top protective layer. The macrofluidic, double-sided adhesive layer is intimately adhered to the skin. The electronic layer is intimately adhered to the macrofluidic, double-sided adhesive layer, as shown in FIG. 4. The microfluidic management layer circumferentially surrounds the at least one electrochemical sensor of the electronic layer. The vapor porous, top protective layer is placed on and completely covers the microfluidic management layer and electronic layer. The vapor porous, top protective layer is intimately adhered to the macrofluidic, double-sided adhesive layer. The fully fabricated sensor apparatus is shown in FIG. 8. Preferably, the length of the apparatus is approximately 76.1 mm. In one embodiment, the adhesive of the apparatus is Double Coated Polyester Nonwoven Tape (commercially available as 3M 9917 as of this writing). In another embodiment, the adhesive of the apparatus is Tan Tricot Knit Tape (commercially available as 3M 9926T as of this writing). The design of the microfluidic layer improves flow control and decreases patch layer delamination during high sweat volume use cases.

Figure 34:
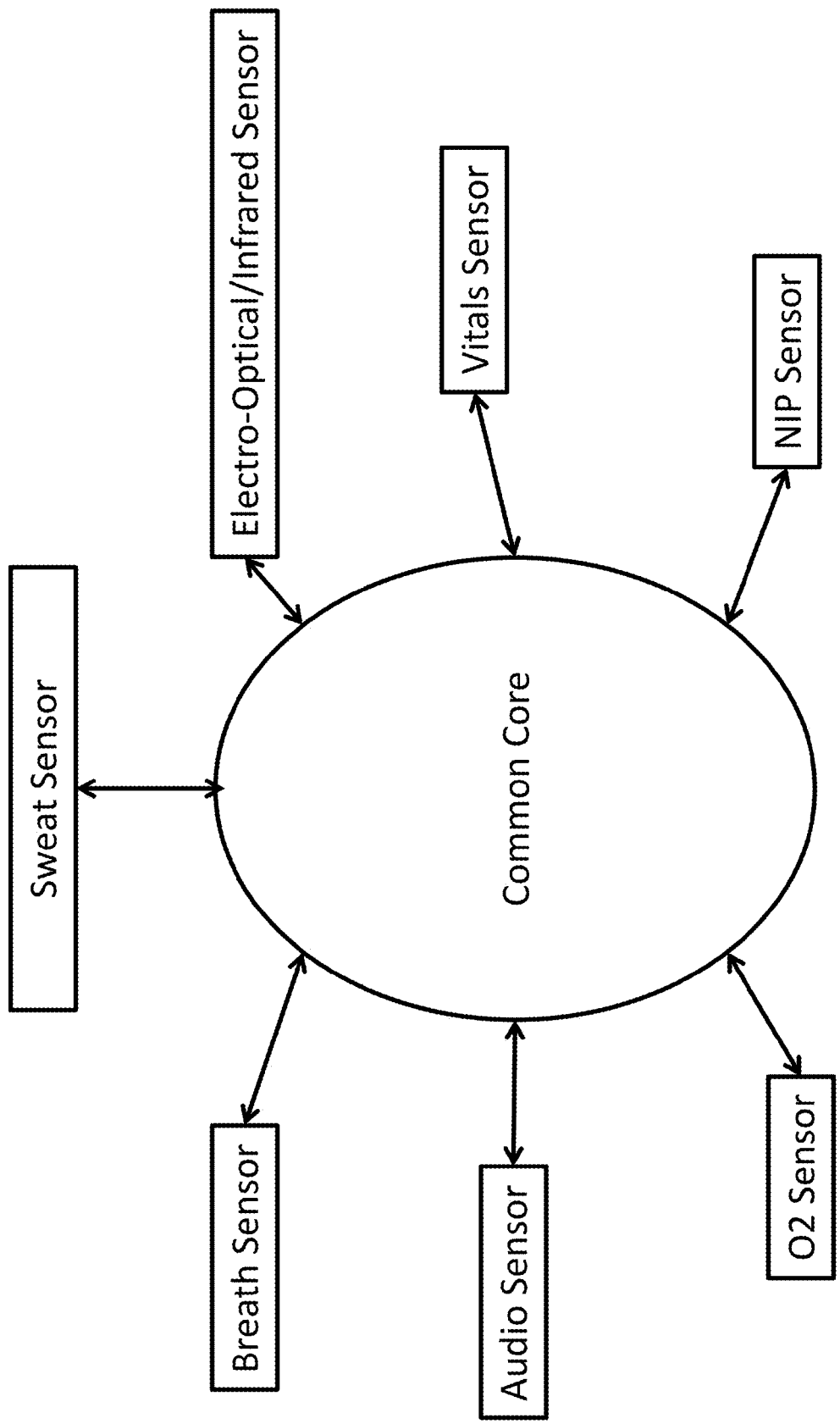
FIG. 34 shows a diagram of a suite of sensors in addition to a sweat sensor.

FIG. 34 shows a diagram illustrating a suite of sensors in addition to a sweat sensor, including a non-invasive penetration (NIP) sensor, an audio sensor, a vitals sensor, an electro-optical/infrared sensor, an oxygen sensor, a breath sensor, and a sweat sensor. In one embodiment the sensor includes at least two of the sensors in FIG. 34. In another embodiment, one of the suite of sensors is the only sensor utilized. One or more of the sensors is embedded in the skin in one embodiment of the present invention. An embedded sensor preferably mimics the composition and behavior of cells. The electro-optical/infrared sensor may include a fluorescent signal sensor. In one embodiment, a reader sends an excitation light through the skin to the biosensor, which then emits a fluorescent light proportional to the amount of biochemical measured.

Figure 35:
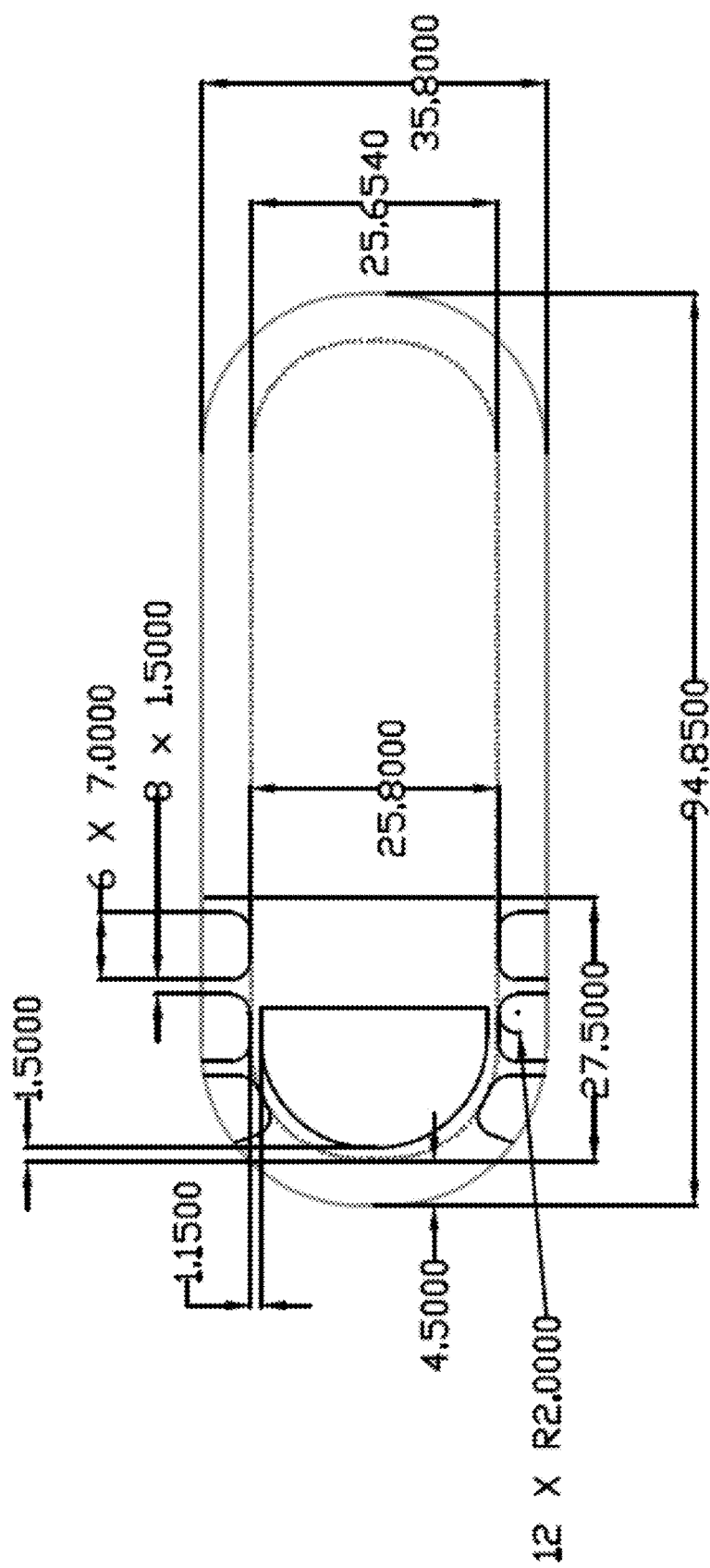
FIG. 35 shows a top perspective view of one embodiment of the sensor apparatus.

FIG. 35 shows a top perspective view of one embodiment of the sensor apparatus. The flex circuit is substantially centrally located on the bandage material and adhesive. Wicking paper is utilized to move bodily fluid, particularly sweat, through the sensor apparatus. The reverse "D" shaped hole is through the adhesive and the wicking paper. All dimensions in FIG. 35 are in MM or VOS, as appropriate.

Figure 36:
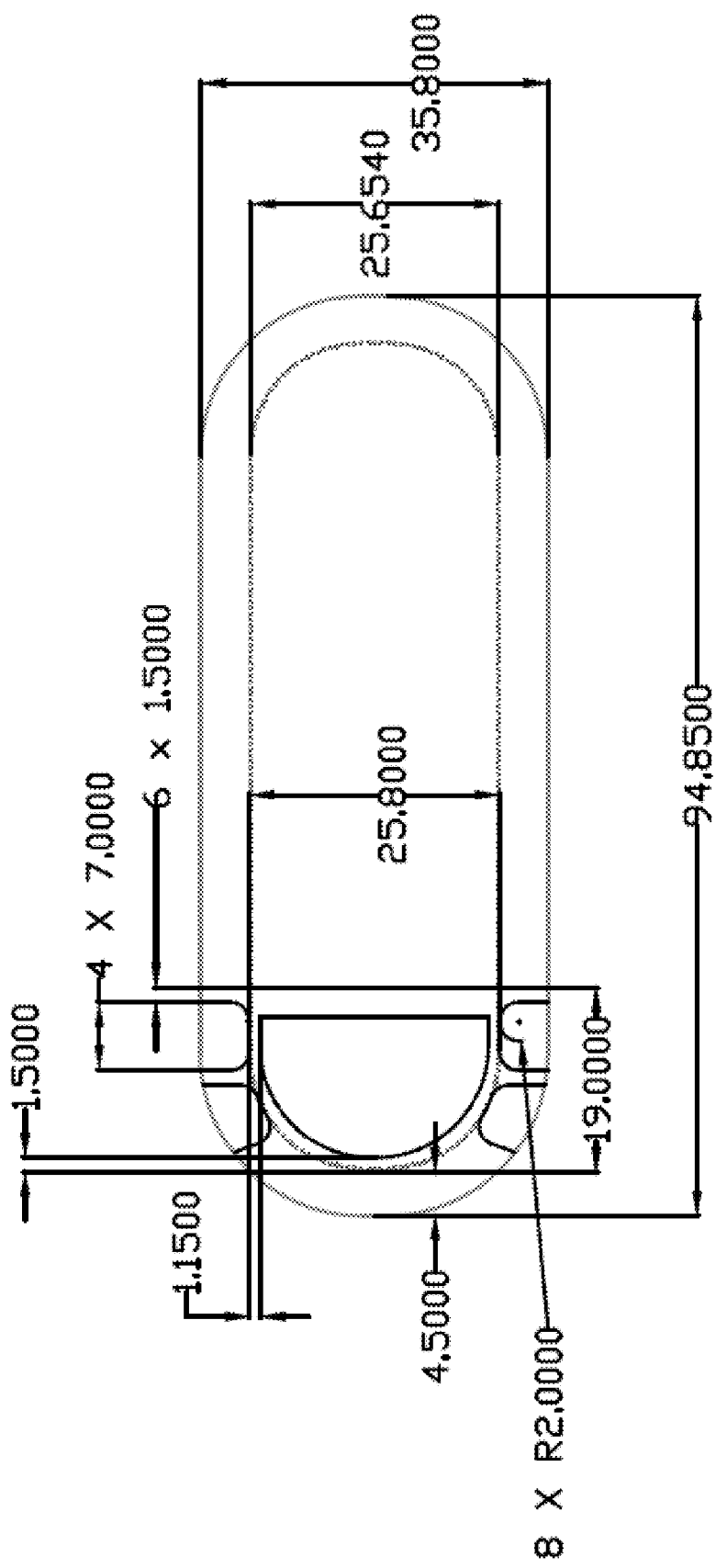
FIG. 36 shows a top perspective view of another embodiment of the sensor apparatus.

FIG. 36 shows a top perspective view of another embodiment of the sensor apparatus. The flex circuit is substantially centrally located on the bandage material and adhesive. Wicking paper is utilized to move bodily fluid, particularly sweat, through the sensor apparatus. The reverse "D" shaped hole is through the adhesive and the wicking paper. All dimensions in FIG. 36 are in MM or VOS, as appropriate.

Figure 9:
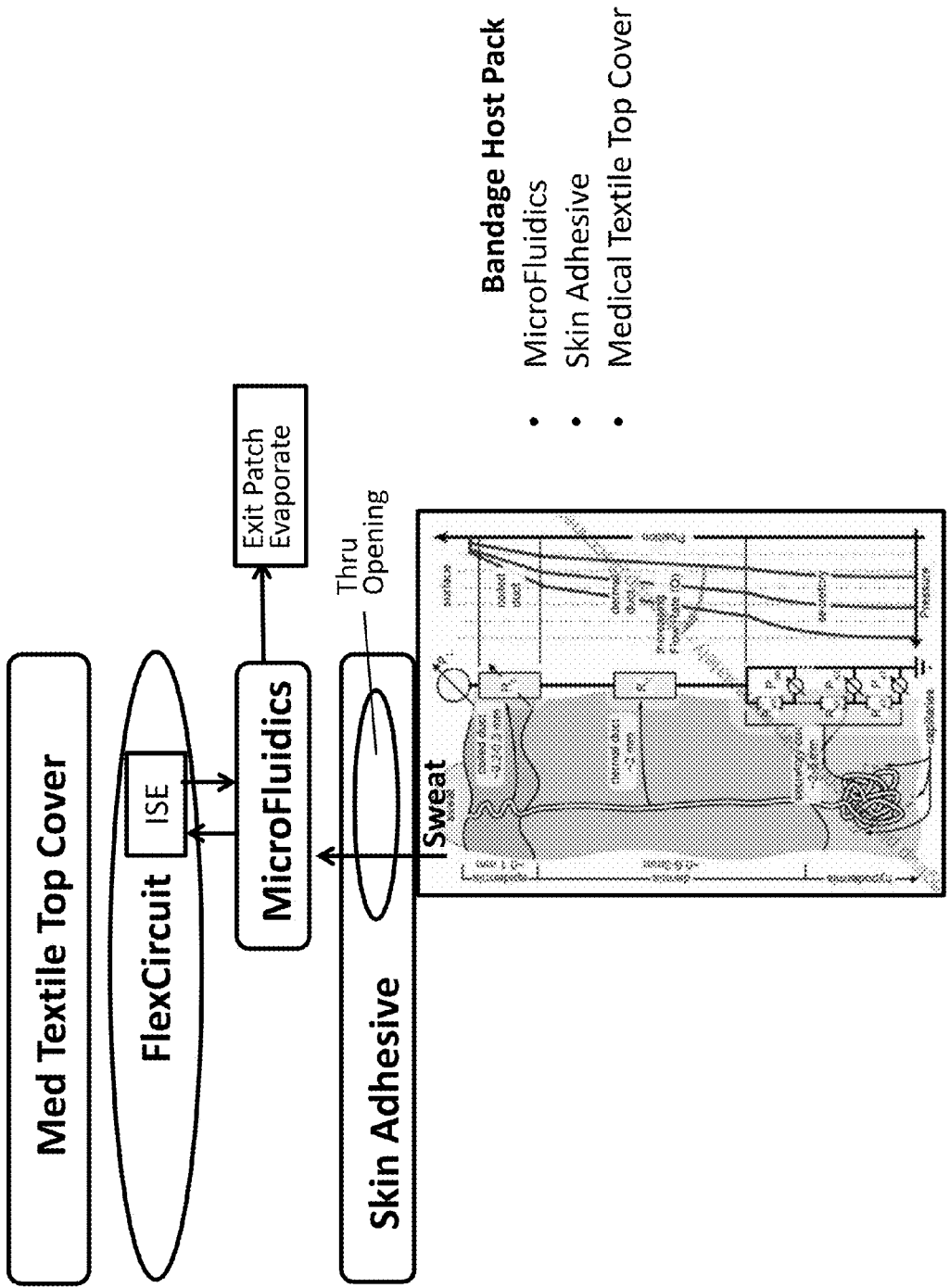
FIG. 9 shows a diagram of the sweat path through the sensor apparatus.

The sensor apparatus is designed to allow sweat to flow through laser cut, macrofluidic pores in the skin adhesive layer, as shown in FIG. 9. Sweat then flows through a filter to the electronics layer, specifically the electrochemical sensor unit, where biomarkers may contact the electrodes of the electrochemical sensor unit. The sweat evaporates through the woven textile protective top layer. The evaporation affords improved and continuous sweat flow into the sensor apparatus. This wicking ensures sweat sensing measures are consistently using new sweat samples rather than static or diluted samples. In one embodiment, the wicking and sweat flow rates range from 0% to 5% Total Body Loss/hr (instant equivalent sweat loss rate) or equivalent to 11.5 L/hr total loss.

The present invention further includes a device with a small amount of ionophore polymer on the active electrodes to filter/prevent untargeted ions to reach the electrode. Sensor functionality and accuracy require precision placement with proper thickness of a small amount of ionophore polymer in one embodiment. The amount is approximately 2 microliters with a designated viscosity placed in a clean assembly environment to completely cover the exposed active electrode on the skin-facing side of the flexcircuit. The coating shall preferably not exceed more than 0.5 mm from the edge of the electrode. In one embodiment, the ionophore polymer is cured. In another embodiment, the curing takes place using heat and/or light to accelerate drying without changing the ionophore selectivity characteristics.

In one embodiment, the sensor is calibrated. Preferably, a user calibrates the sensor using actual test results and feedback from the sensor.

Figure 7:
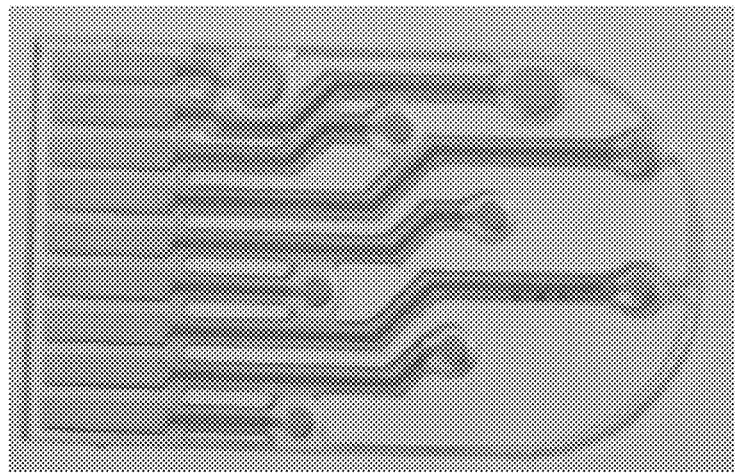
FIG. 7 shows the electrochemical sensors.
Figure 10:
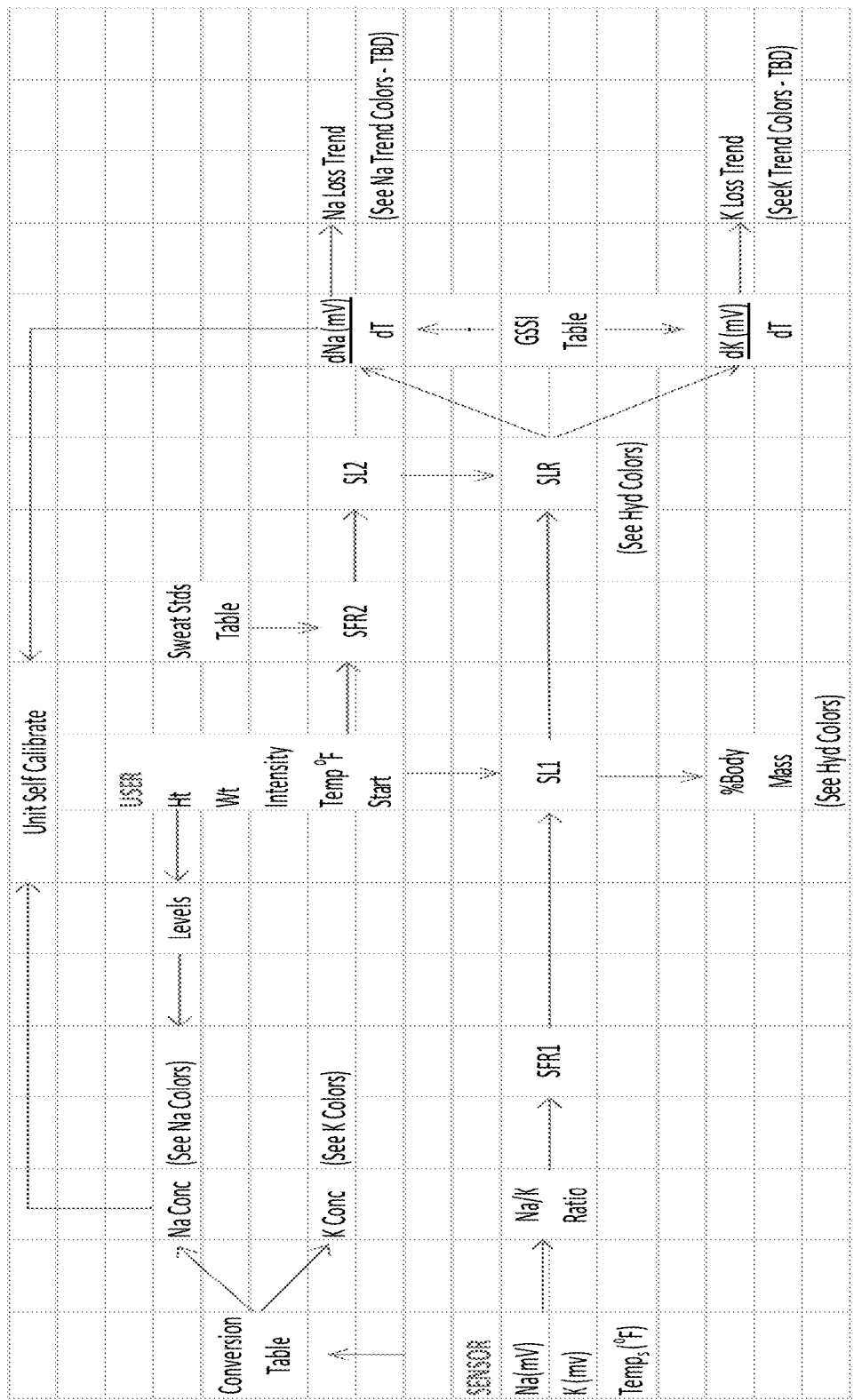
FIG. 10 shows a diagram of the analytical process within the sensor apparatus.
Figure 15:
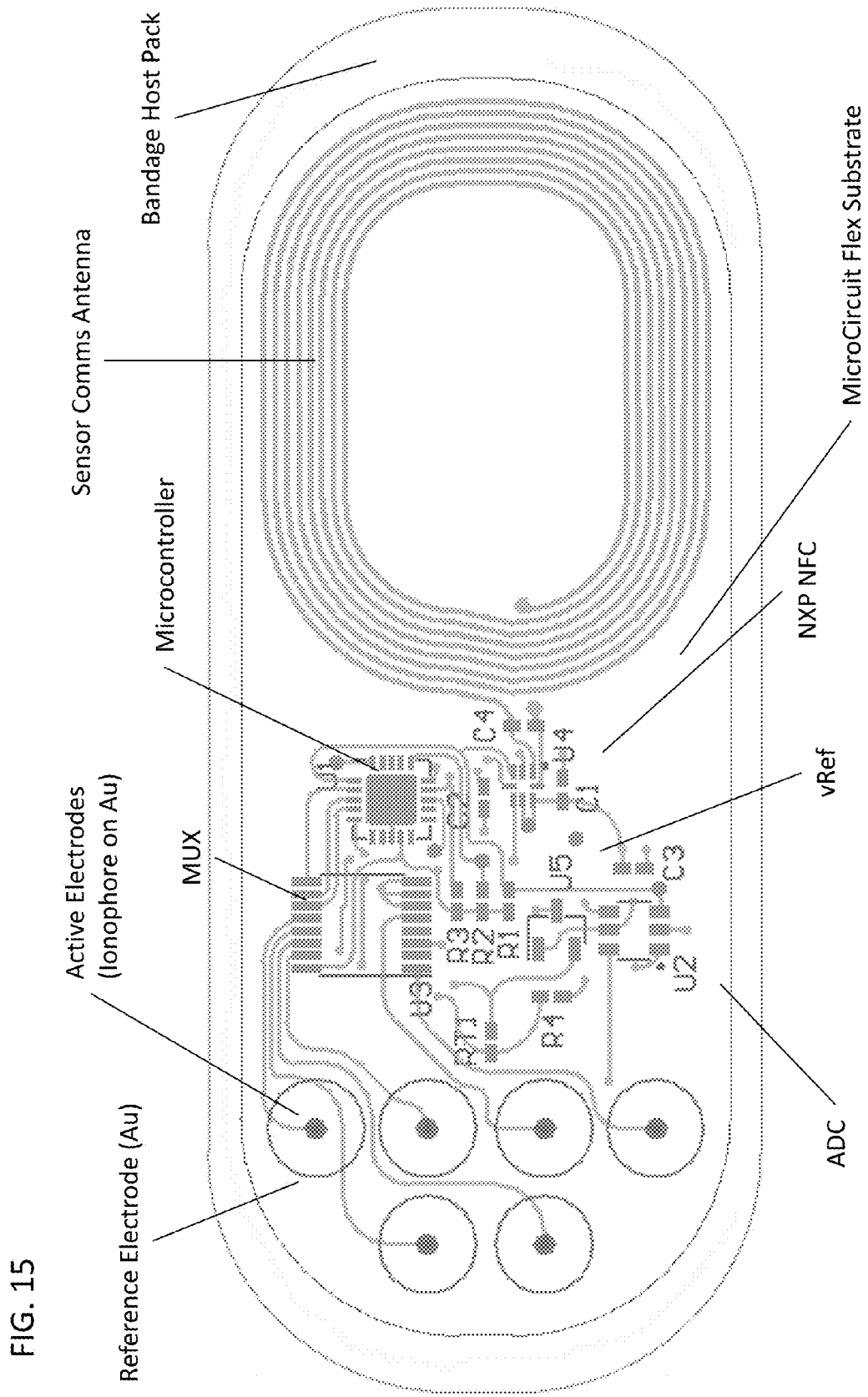
FIG. 15 shows a diagram of components within the sweat sensor subsystem.
Figure 17:
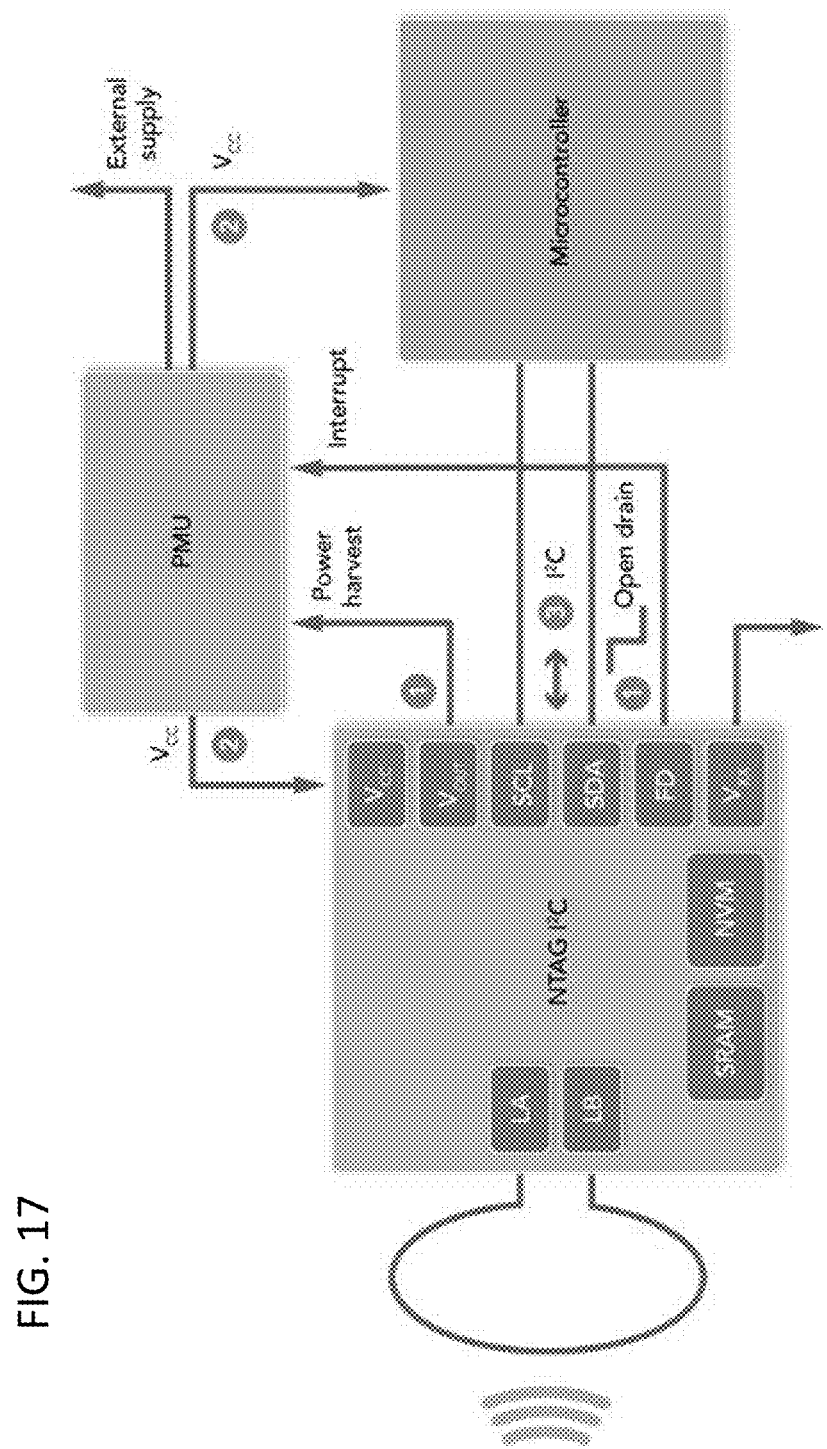
FIG. 17 shows a diagram of a NXP semiconductor used in an embodiment of the sensor apparatus.
Figure 18:
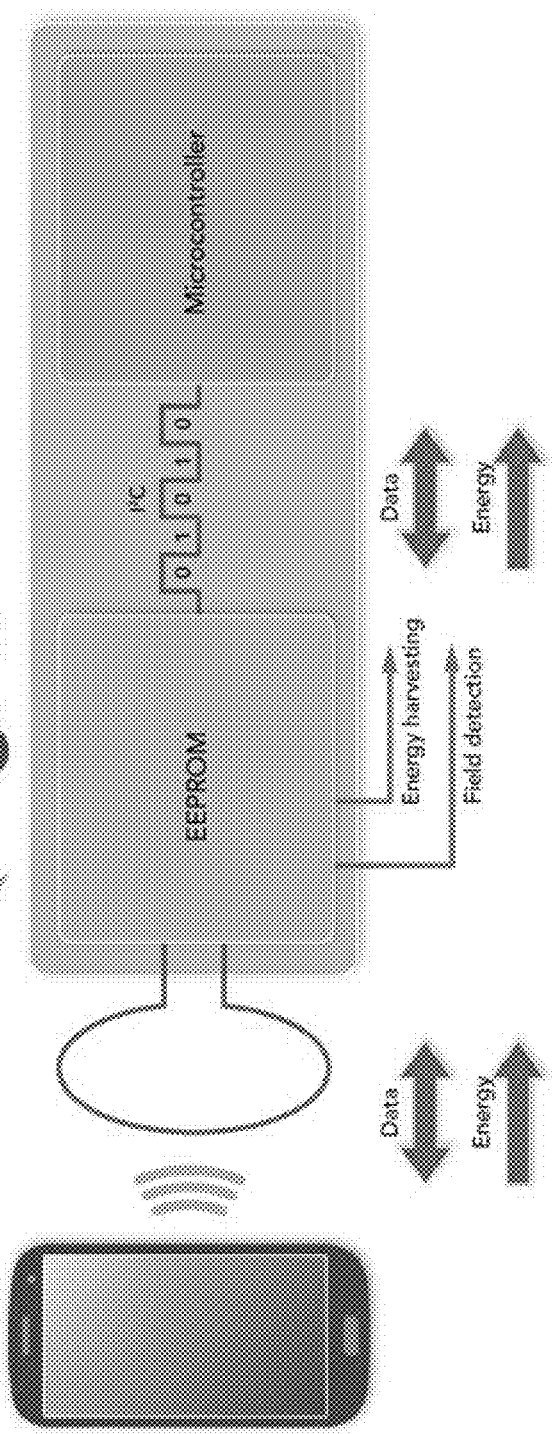
FIG. 18 shows a diagram of the communication between a NXP semiconductor and a wireless device in an embodiment of the sensor apparatus.
Figure 19:
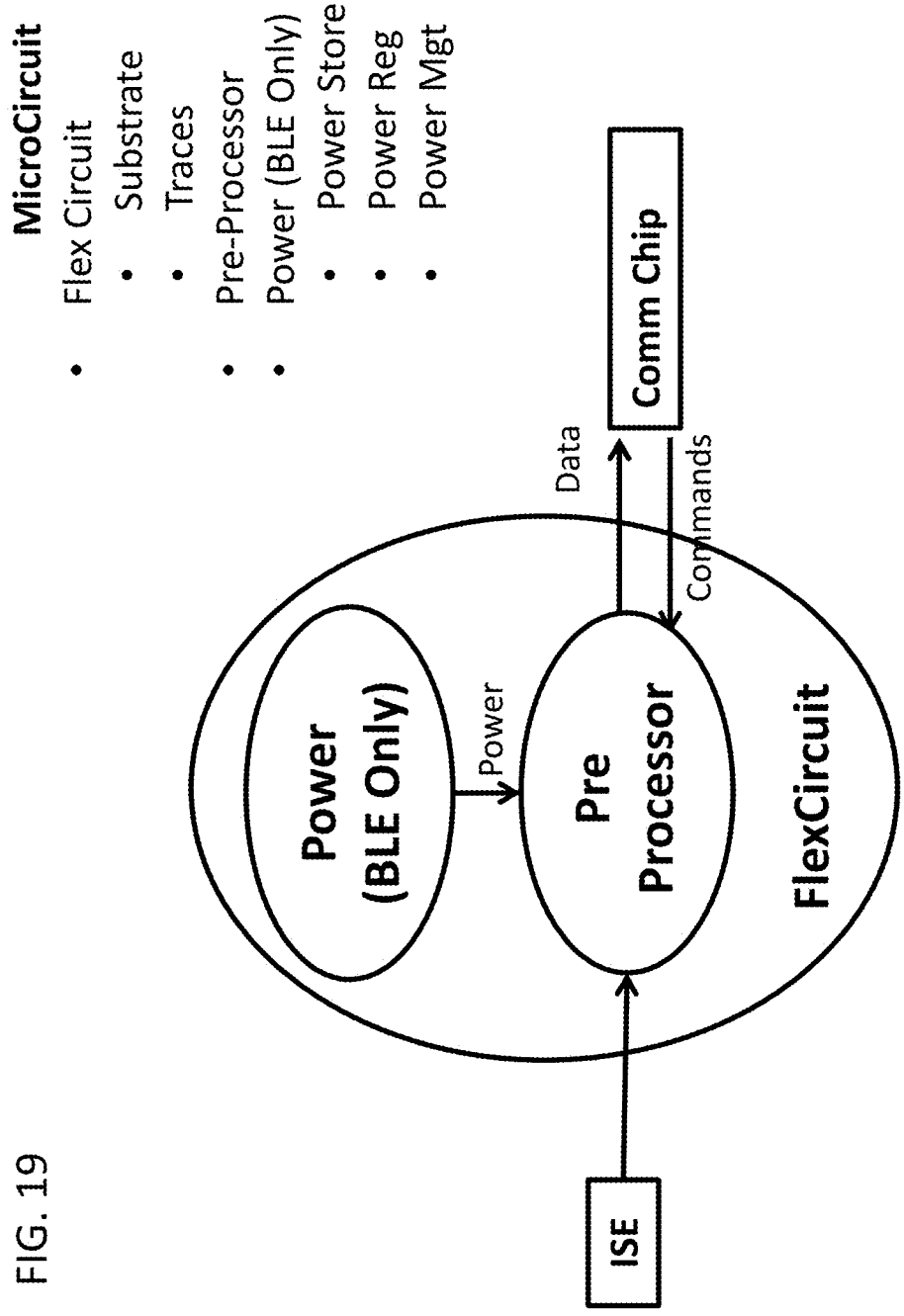
FIG. 19 shows a diagram of a sweat microcircuit of the sensor apparatus.

The sensor apparatus includes sweat sensor subsystem, as shown in FIG. 15, which includes a microcontroller that receives multiple input data, which are input from multiple sources. A first source is biological fluid, preferably sweat, although alternative fluids may be used. The sweat contains a variety of analytes, such as, by way of example and not limitation, electrolytes, small molecules, proteins, and metabolites. Exemplary analytes include substances including sodium or potassium. In one embodiment, the sensor apparatus is operable to sense sodium in a dynamic range from about 0 mM to about 120 mM, with normal ranges in humans being about 20 mM to about 100 mM. In another embodiment, the sensor apparatus is operable to sense potassium in a dynamic range from about 0 mM to about 40 mM, with normal ranges in humans being about 5 mM to about 20 mM. In one embodiment, the sensor has a response time of about 60 seconds with about a 90% response. Other analytes include oxygen, glucose, ammonium, and interleukins. In one embodiment, the sensor is operable to analyze the analytes at a pM level, preferably in the 1-10 pM range or even below 1 pM (the sub-pM level). These analytes are collected at the electrochemical sensor, as shown in FIG. 7, which houses reference (preferably standard) and active electrodes, wherein, by example and not limitation, the electrodes are silver, zinc, copper, gold, platinum, rhodium, carbon or a combination thereof. In one embodiment, the apparatus has an embedded dot-circle configuration for a reference electrode to improve stability through less interference. Additionally, gold probes or electrodes are used in one embodiment to improve stability and reduce production costs. The apparatus also includes a microprocessor, multiplexer (mux), ADC, and optimized on board processing for real time, pre-transmission sensor signal conditioning in another embodiment. The apparatus is also optimized for efficient and successful transmission during athletic usage. When the electrodes contact the sweat biomarkers a voltage is produced. Three electrodes per analyte are used to create an average voltage value, which is transmitted to the microcontroller, wherein the microcontroller pre-processes and prepares the sensor data to be communicated to the transceiver device via Bluetooth communication in preferred embodiments. Alternatively, an RFID, NFC, or other proprietary communications chip may be provided. The NFC chip preferably has an increased base signal amplitude for better processing and lower resolution as well as better concentration confidence and resolution. Bluetooth is preferred due to its low energy, ubiquitousness, and low cost. Most any Bluetooth enabled device can pair with another Bluetooth device within a given proximity, which affords more ubiquitous communication between the microcontroller and a transceiver device. The dynamic and automatic connections of Bluetooth allow for multiple microcontrollers to communicate with a single transceiver device, which, by way of example and not limitation, would provide for a team-based situation, wherein the sweat data of multiple athletes is communicated to a single coach or team database. A second source of input data is the remote transceiver device. By two-way communication, the transceiver device may transmit data to the microcontroller of the apparatus, which is part of an inter-integrated circuit, as shown in FIGS. 17 and 18. The data to be transmitted will have been manually or automatically input in the transceiver device. For example and not limitation, as shown in FIG. 10, types of manually input data of the one or multiple users may include gender or gender factors, fitness or conditioning level, age, and anthropomorphic data, such as height and weight. The anthropomorphic data is preferably used to estimate user body surface area, which is a critical variable for accurately determining sweat loss and electrolyte loss. More preferably, estimates are a product of anthropomorphic data, gender, and age. Prior art assumes a body surface area of about 2 m$^2$ to calculate sweat loss and electrolyte loss. Using anthropomorphic variables, as in the present invention, consistently decreases calculated error rate from between about 50 and about 70 percent to less than about 10 percent, preferably. The accuracy resulting from body mass estimation revealed that persons with larger body mass, such as males, more readily adapt to physical exertion by sweating more quickly, a larger volume, and lower electrolyte concentration. Similarly, a physically fit person with a small body mass, such as a female, adapts to physical exertion by adjusting sweat flow rates and electrolyte levels. Although prior art has validly analyzed sodium, potassium, sweat rates, etc., it has failed to account for body surface area, mass, and VO2 max, thus inflating calculated error rate. These data support that sweat flow rates and electrolyte loss is strongly correlated with body size and surface area and conditioning level, which further supports the need for proper estimation of body size, such as through anthropomorphic variables.

Other types of manually input data include metabolic disorder, such as diabetes. Since Type 1 diabetes is associated with reduced eccrine gland activation and, thus, lower sweat rates, the present invention may reveal user metabolic disorder. Further, automatically input data may include user skin temperature, outdoor or indoor temperature, and/or humidity and altitude. The automatically input data may be generated in the remote transceiver device by integrated applications, such as GPS or weather. Together, the data transmitted to the microcontroller from the remote transceiver device represent modifying variables.

Figure 11C:
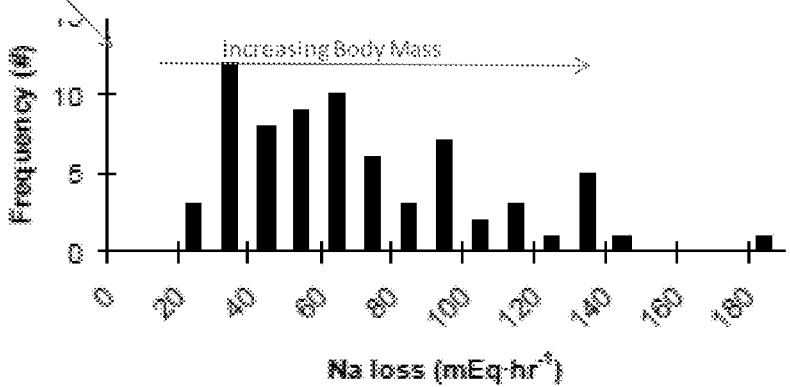
FIG. 11C shows tables including work level, zone, SFR, mV ratio, Na Loss, K Loss, Typ Wt, sweating rate and sweat sodium concentration and a chart of frequency vs. Na loss.
Figure 14:
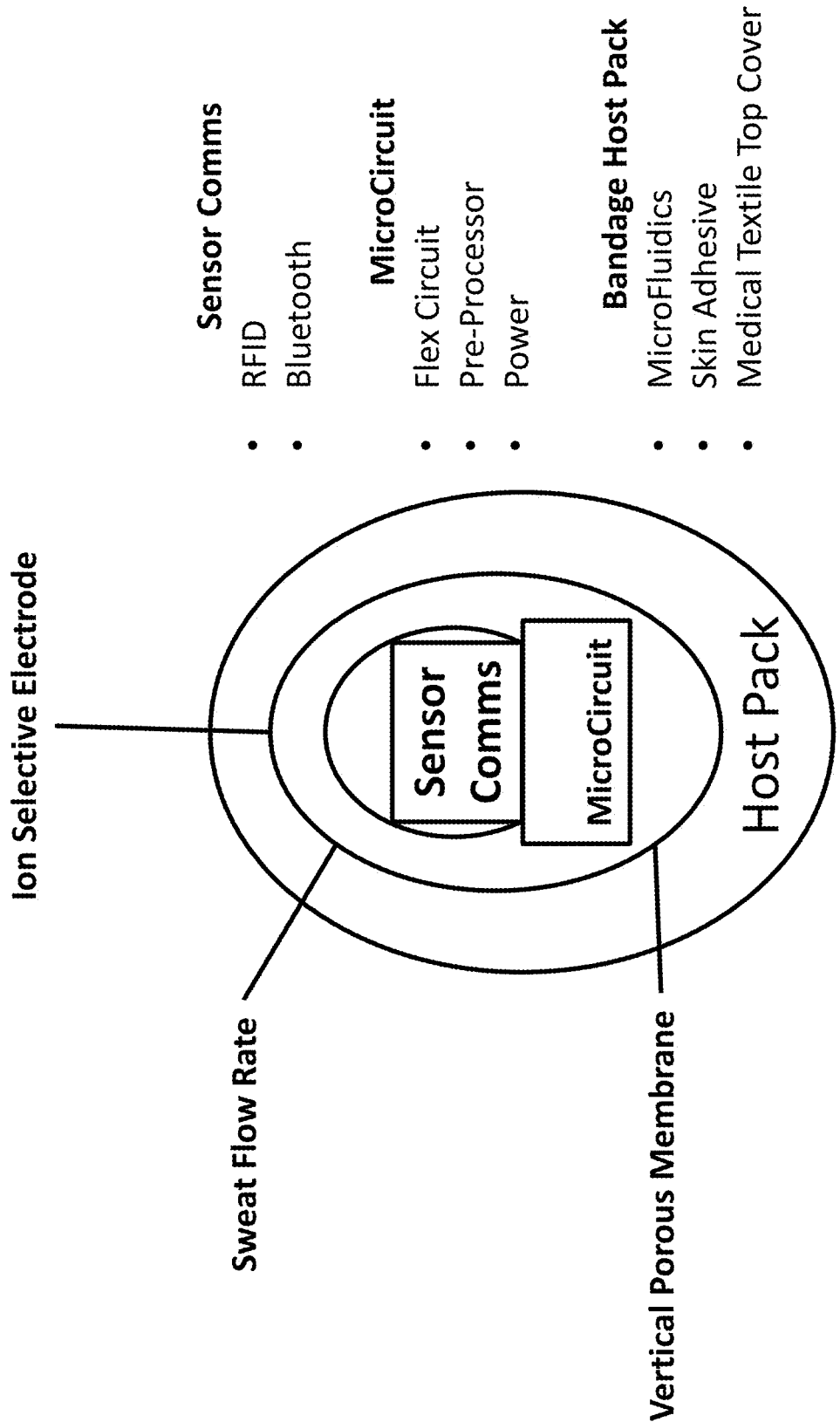
FIG. 14 shows a diagram of the sweat sensor subsystem.

The microcontroller converts the voltage data from the biological fluid into a concentration or ratio value of the biomarker using at least one programmed algorithm. For example, as shown in FIG. 11A, if the algorithm was converting the amount of sodium ions detected at the sensor into a sodium concentration, the algorithm would apply around 0.242 mM per mV of sodium. For potassium conversion, the ratio would be around 0.195 mM per mV of potassium. Embodiments for sensing sodium and potassium concentration in a liquid, including sweat, are disclosed in U.S. Pub. No. 20150057515, which is incorporated herein by reference in its entirety. In one embodiment, the sweat rate based sodium and potassium ratios of U.S. Pub. No. 20150057515 are included in algorithms of the present invention. In one embodiment, sensor data are inputs into real time blood serum hydration, sodium concentration, and potassium concentration using absorption and extraction models that use sensor data as starting points. These calculated values are the apparatus' output data. Types of output data include but are not limited to concentrations, such as molarity, osmolarity, and osmolality, and descriptive statistics, such as averages, ratios, and trends, all of which may be categorized based on a sub-range within a larger physiological range of the biomarker, as shown in FIG. 13A. The modifying variables transmitted from the remote transceiver device may modify the algorithm, which may adjust the output data.

The output data is then transmitted from the apparatus to a remote computer device, such as by way of example and not limitation, a smartphone, a tablet computer, or wearable computer, preferably, through wireless network communication by the transceiver antenna (which may include a coil) of the apparatus. Using a larger antenna in the present invention provided for lower data loss and easier reads associated with a broad x-y placement tolerance. The wireless transmission is provided by any suitable wireless communication, wireless network communication, standards-based or non-standards-based, by way of example and not limitation, Bluetooth, radiofrequency, zigbee, near field communication, or other similar commercially utilized standards. At the remote transceiver device, the output data can be viewed and assessed by the one or multiple users. The one or more users also may manipulate or further analyze the output data, such as by creating user defined graphs and tables. Preferably, the remote transceiver device is portable.

Figure 16:
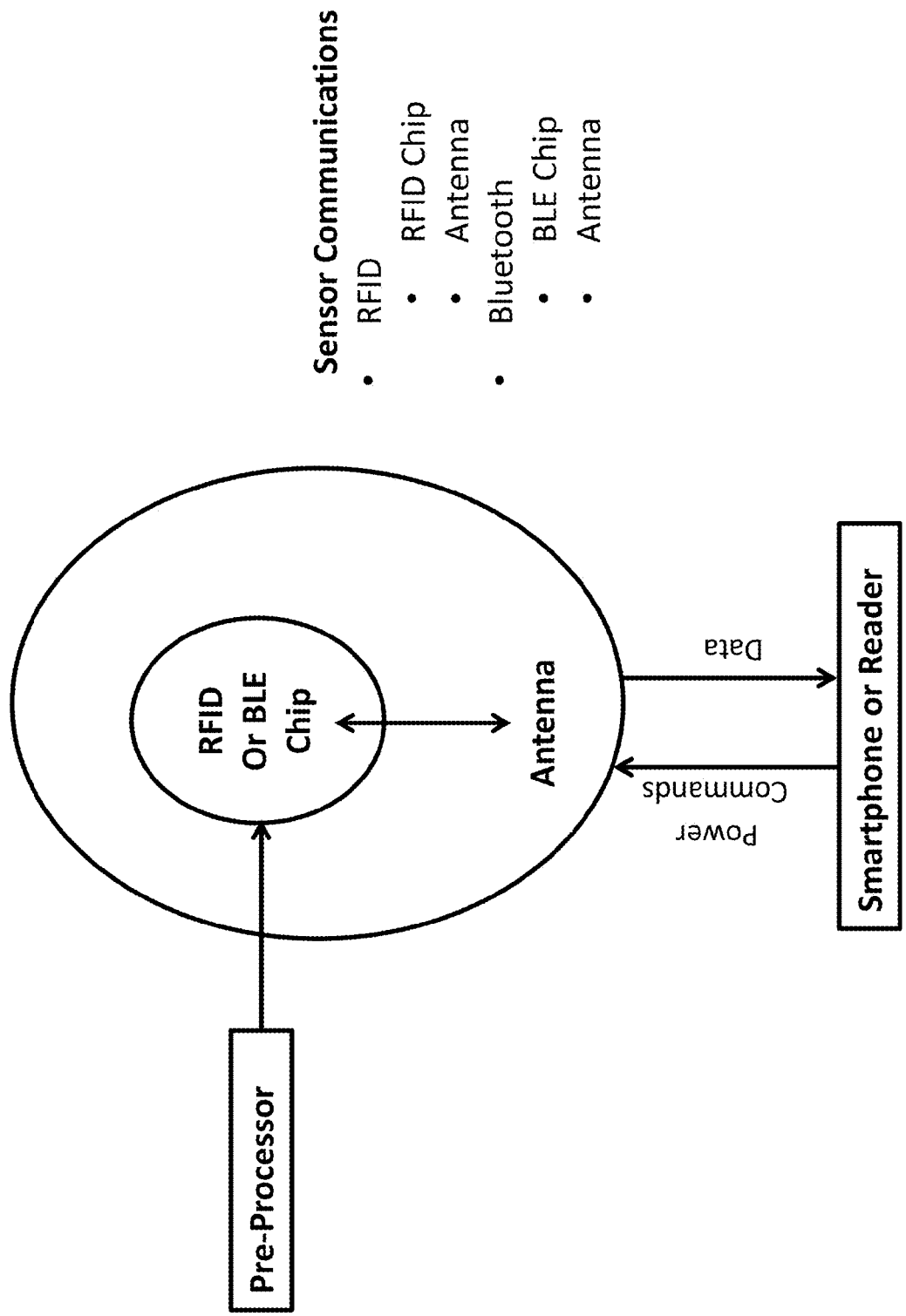
FIG. 16 shows a diagram of sweat sensor communications.

More preferably, the device is a smartphone. Alternative devices include bulk readers, such as food and or beverage dispensers with sensor and/or mobile app communication capabilities or athletic training gear including treadmills, spin bikes, ellipticals, stair climbers, and weight machines with integrated mobile communication capabilities. More alternative devices include desktop or laptop computers and tablets. FIG. 16 diagrams the communication between the sensor apparatus and the smartphone or reader, wherein power, commands, and/or data may be communicated.

From the remote transceiver device, the user may transmit processed or unprocessed data to at least one remote computer server, preferably by wireless communication, such as through a user web service. The remote computer server, which may be a network or cloud, may store the transmitted data in a library. The cloud preferably serves as a software development kit (SDK) for potential solution partners, a cloud based user app (with real time ingestion, calculation, and display), and a cloud based user store with ubiquitous access.

Figure 29:
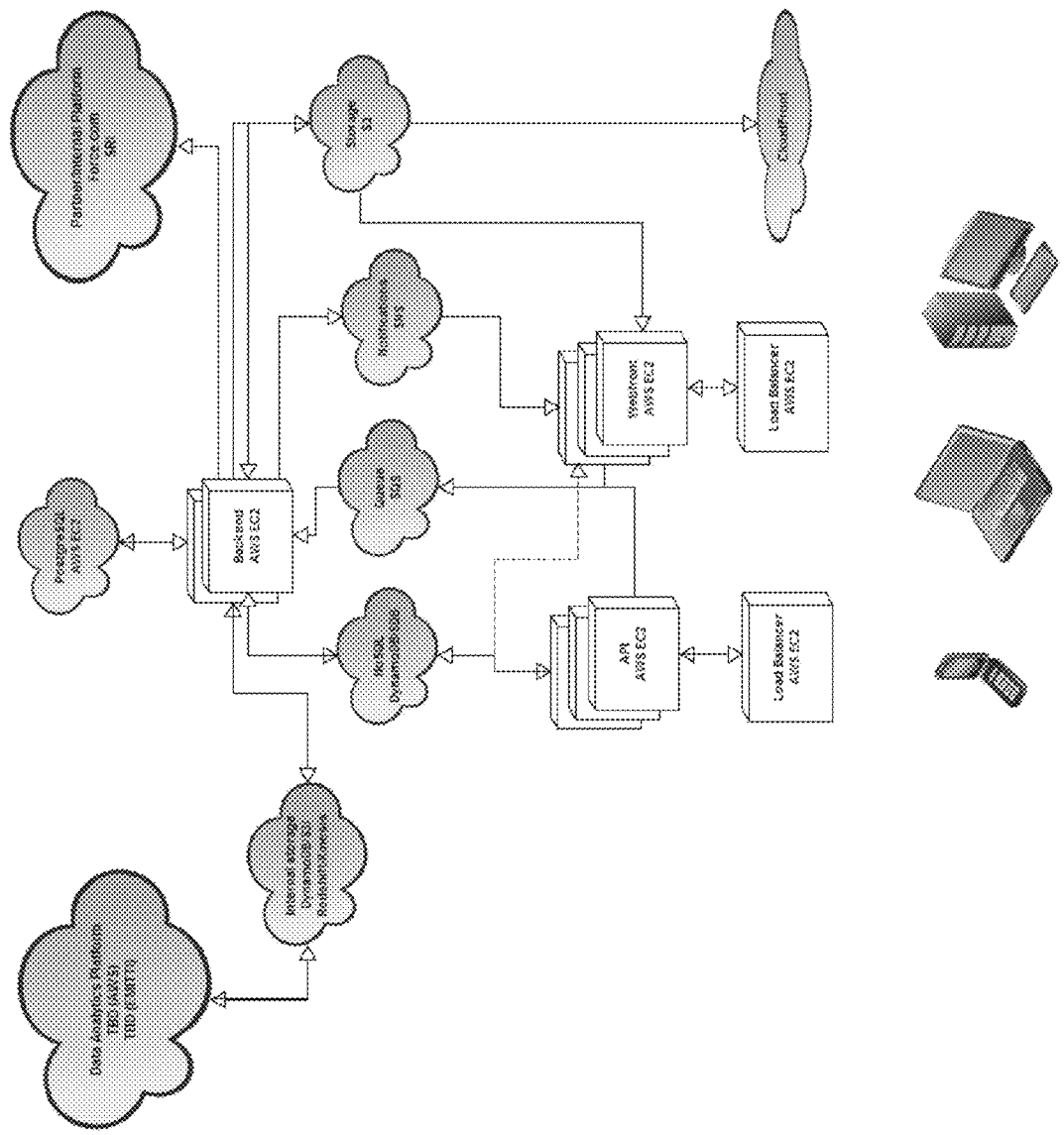
FIG. 29 shows a diagram of a cloud enterprise.

The library will include functions, such as file storage, security, extensions, utilities, scheduling, messaging, persistence, cache, and logging. FIG. 29 shows a cloud enterprise, wherein a cloud computing platform receives data from application users and processes it for internal and partner use. The software code that resides in a cloud-based computer system of the present invention is designed, constructed, and configured to handle the unique data in unique ways. It automatically validates data (to determine if it is reasonable/useable data) and triggers a series of workflows based on the type, date/time stamps, and scope of data to correlate and identify trends. It further includes correlation and trending tags for subsequent user alerts/analysis. The code has an open framework built on web service concepts to interact and integrate with other $3^{rd}$ party analytics. These web service calls are a series of open Application Programming Interfaces (APIs) aggregated into a Software Development Kit (SDK) which enables authorized $3^{rd}$ party developers to create and maintain $3^{rd}$ party user apps that leverage the cloud infrastructure to access/share data, correlations, trends, and other analytic results.

The two-way communication between the apparatus and the remote transceiver device is significant for the fullness of system functionality. As shown in FIG. 16, the remote transceiver device may communicate with the apparatus to provide, by way of example and not limitation, commands, electrode calibration, microcontroller software updates, new or updated algorithms, and/or new or updated modifying variables for algorithms. Communication may be manually or audibly activated. The apparatus may communicate with the remote transceiver device to provide, by way of example and not limitation, output data, microcontroller health properties, error codes, electrode maintenance or malfunction. At the transceiver device, the one or more users may separately or simultaneously view selected session tables, full history session tables, sensor or multi-sensor chronology, and external sensor correlation. Further, selected biomarker or multi-biomarker histories may be viewed.

Figure 20:
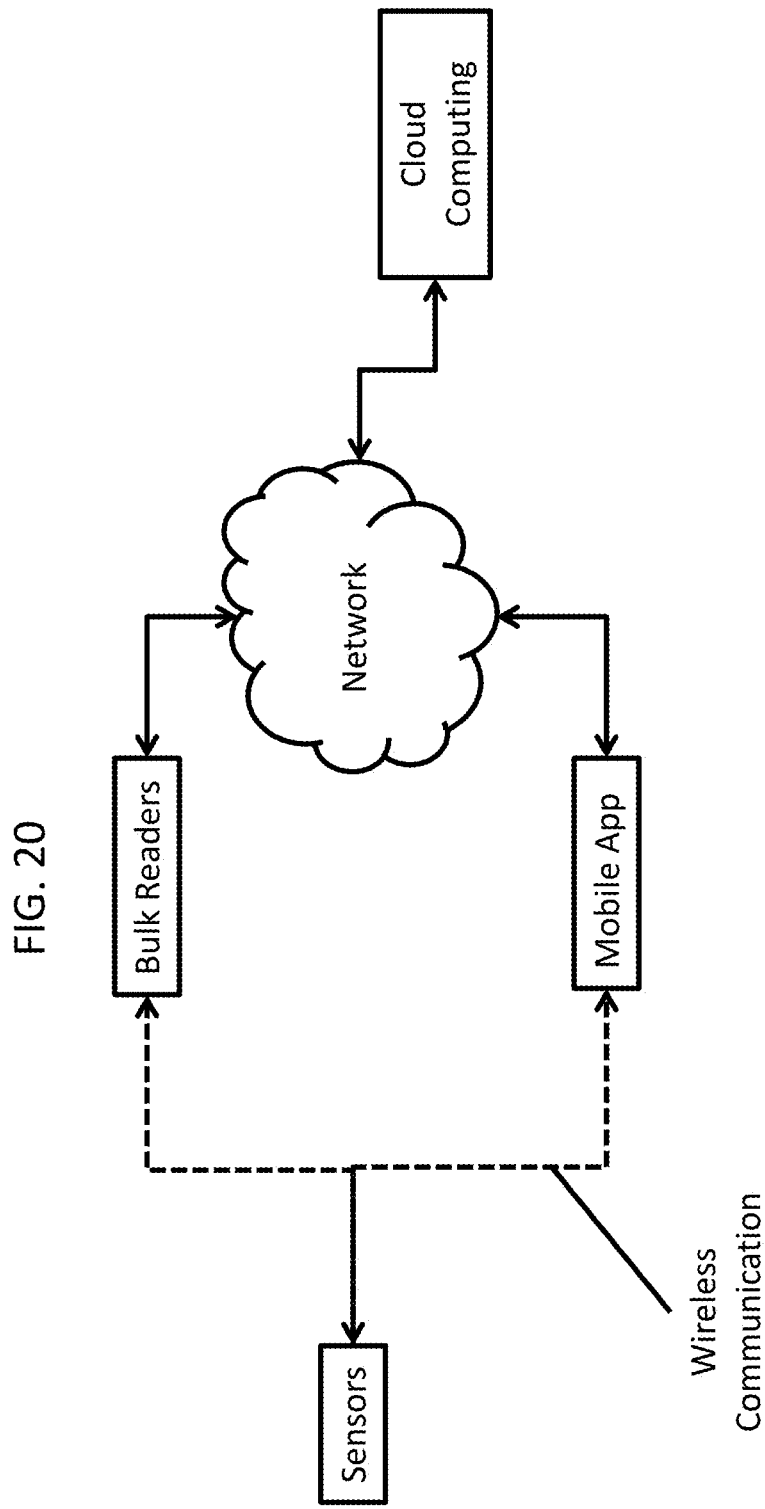
FIG. 20 shows a diagram of the system architecture.
Figure 21:
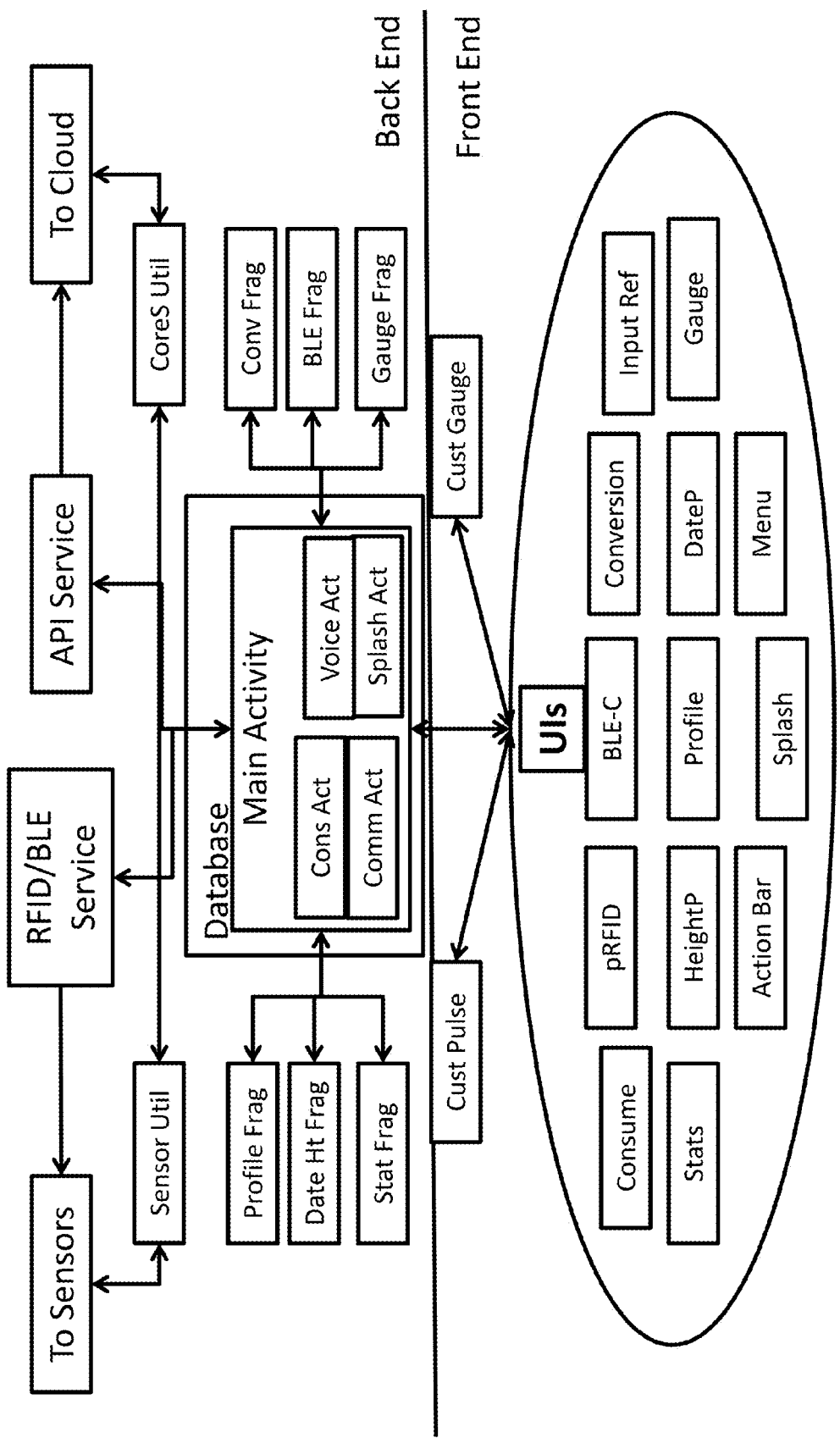
FIG. 21 shows a diagram of the controls within the user mobile app of the wireless remote transceiver.
Figure 22:
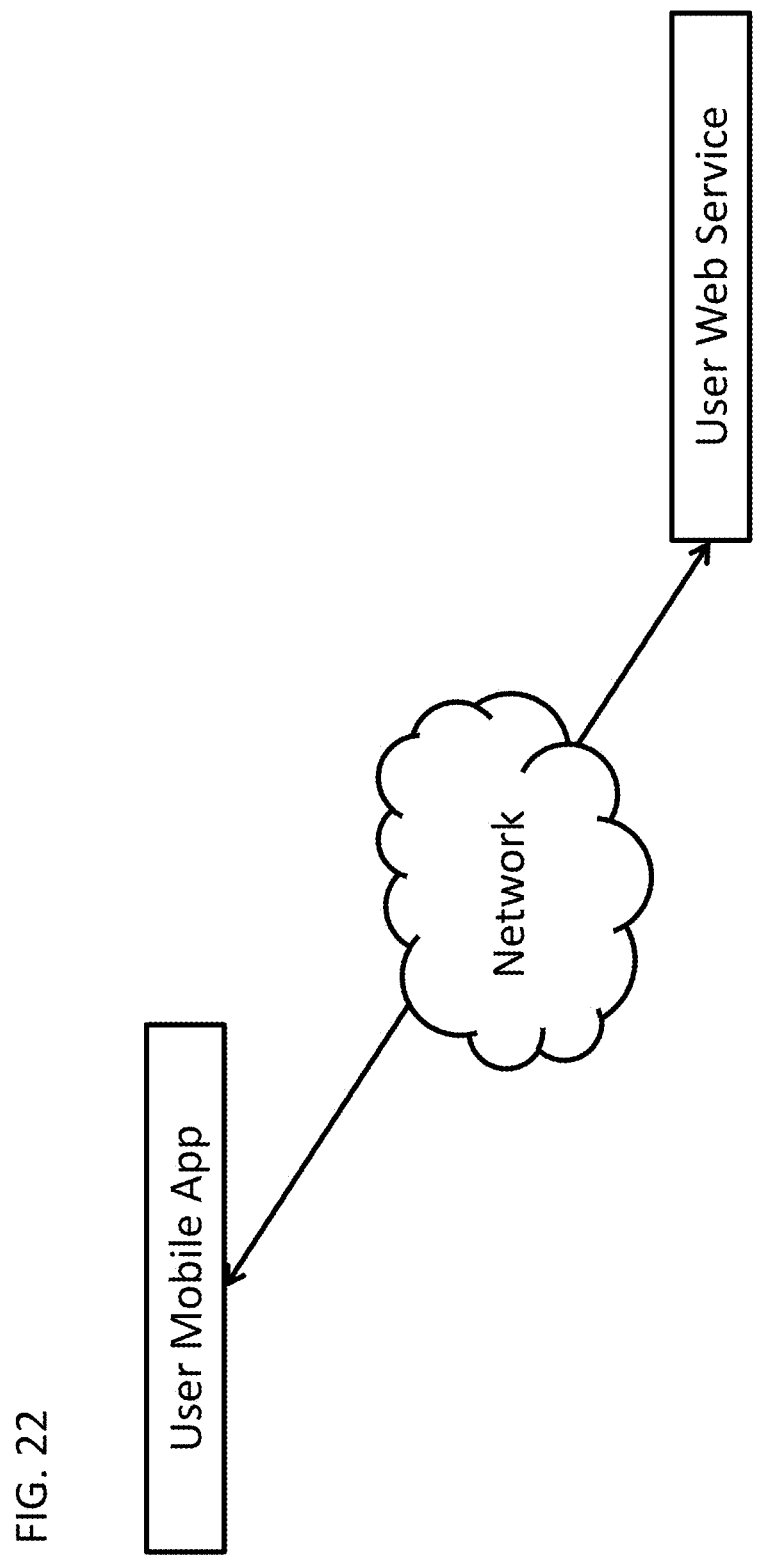
FIG. 22 shows a diagram of the network connection between the user mobile app and the user web service.
Figure 23:
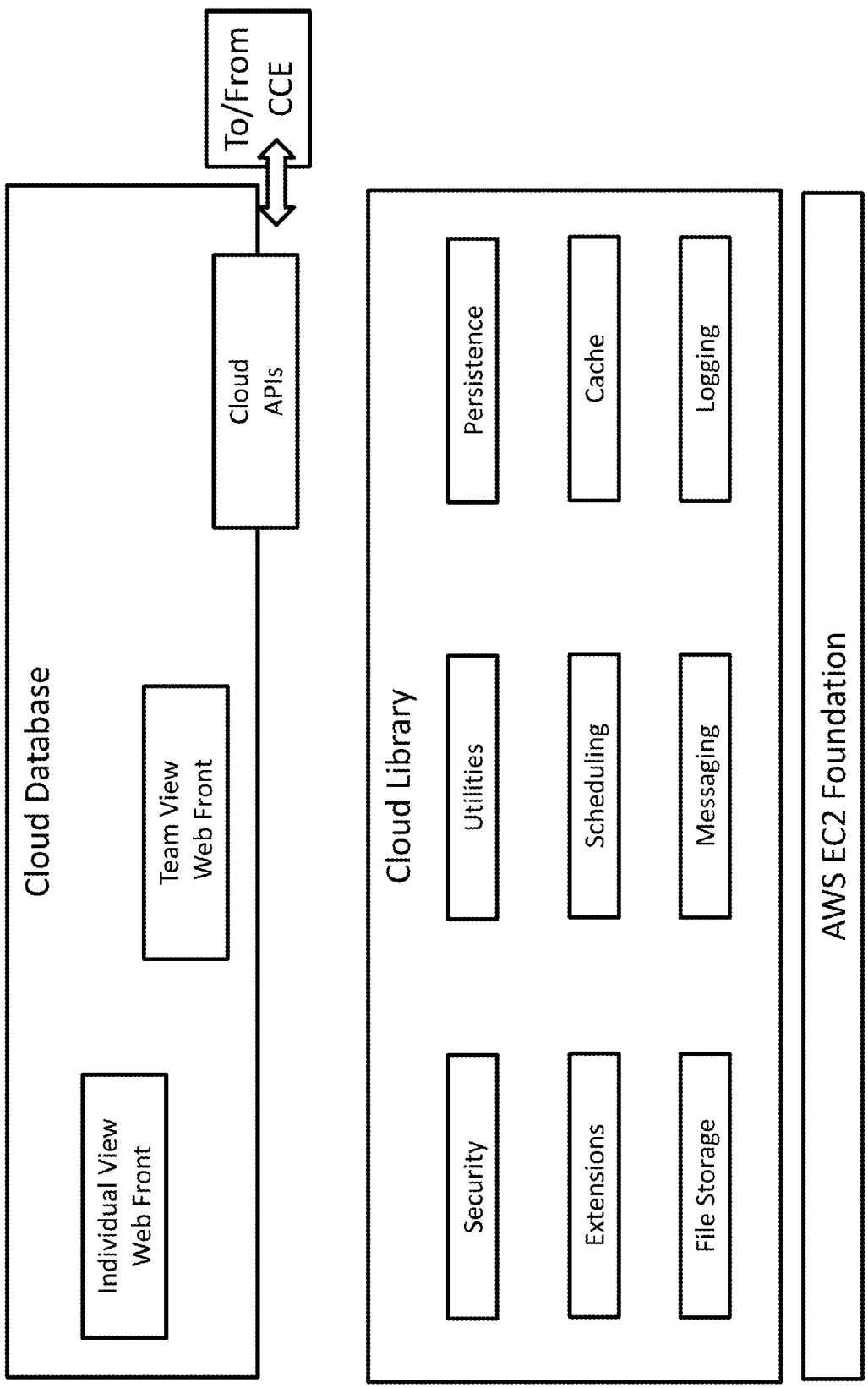
FIG. 23 shows a diagram of the controls within the cloud database and library, which are part of the user web service.
Figure 24:
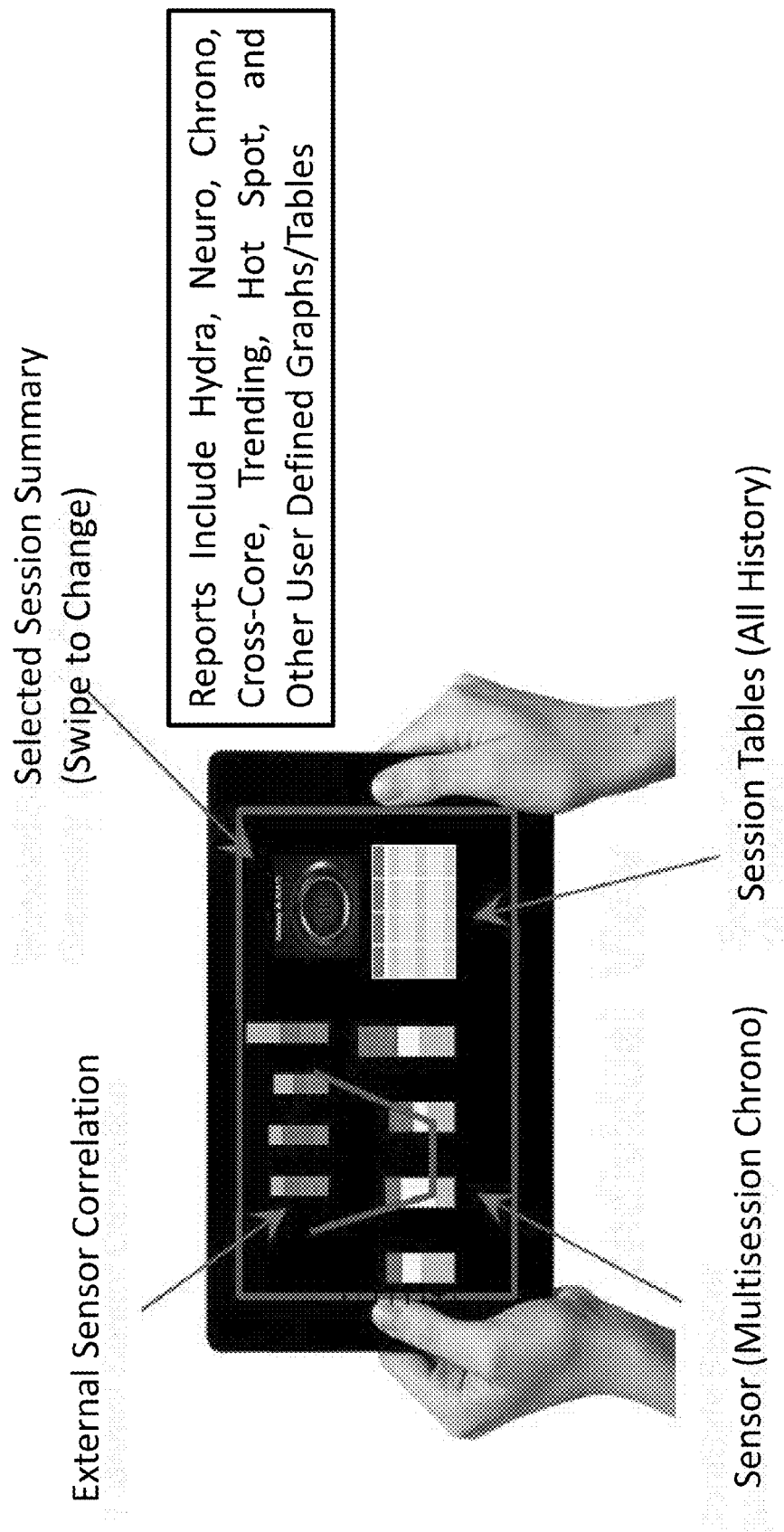
FIG. 24 shows an individual view of the user web front.
Figure 25:
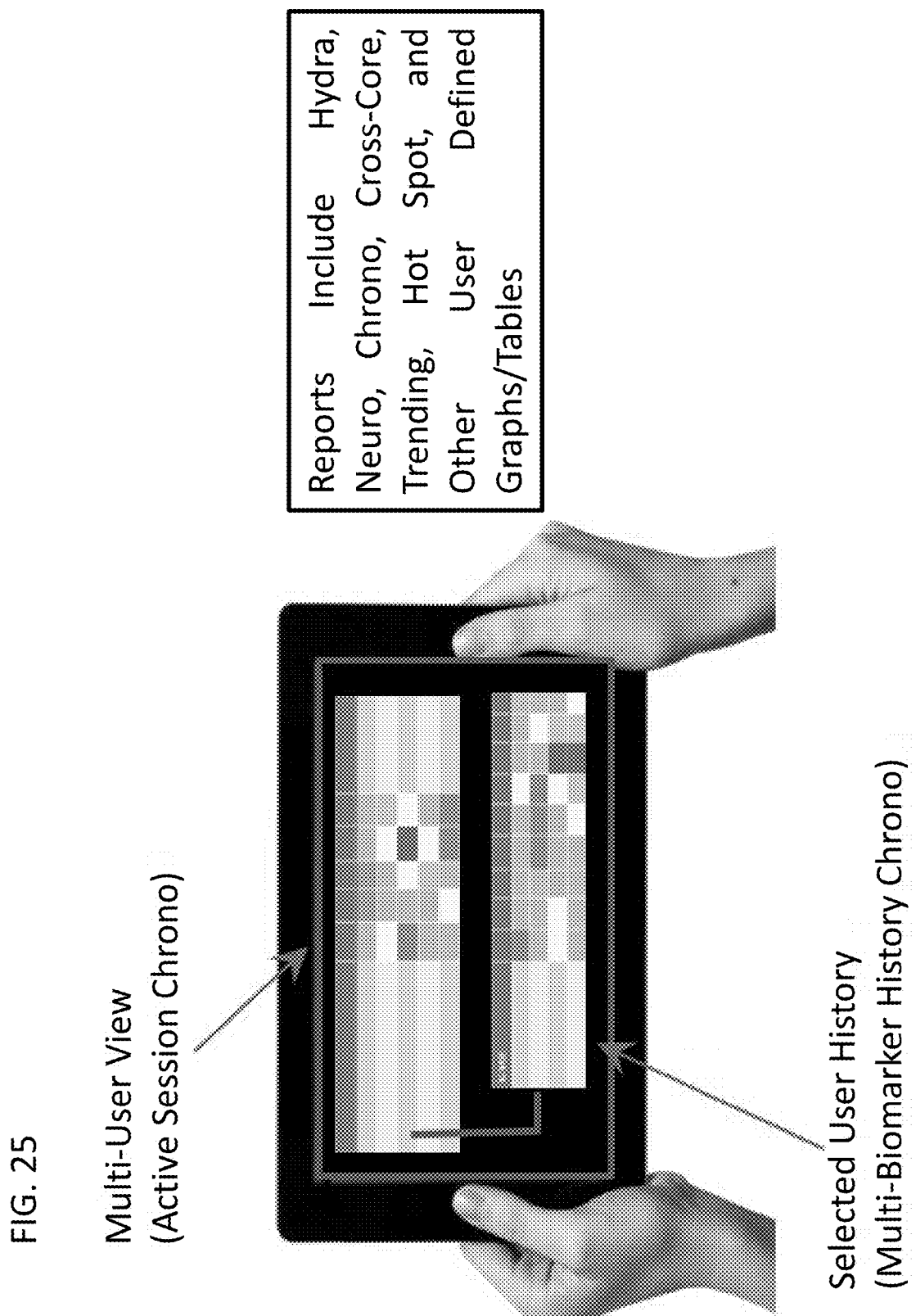
FIG. 25 shows a multi-user view of the user web front.
Figure 26:
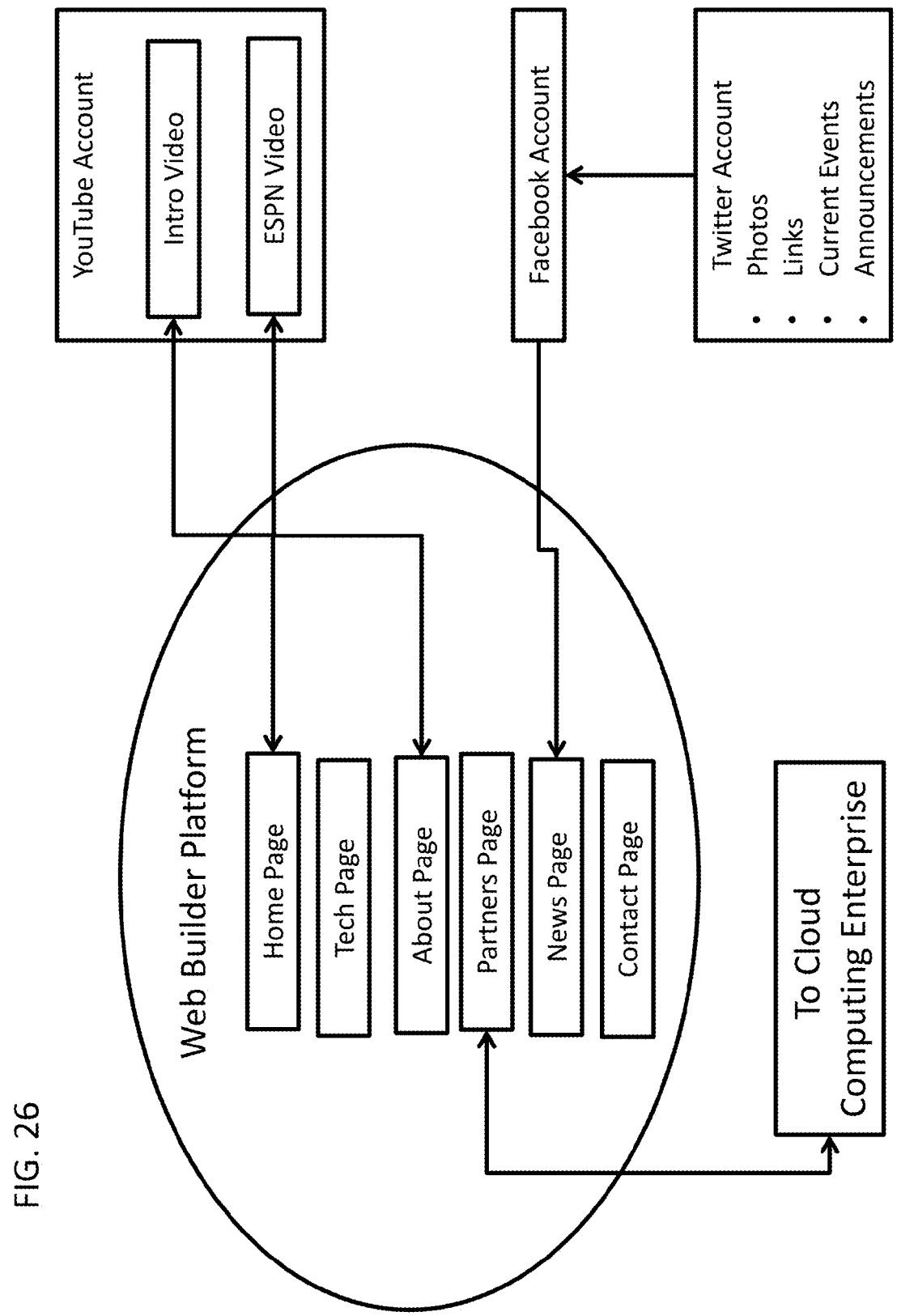
FIG. 26 shows a diagram of the controls within the present invention's website.
Figure 27:
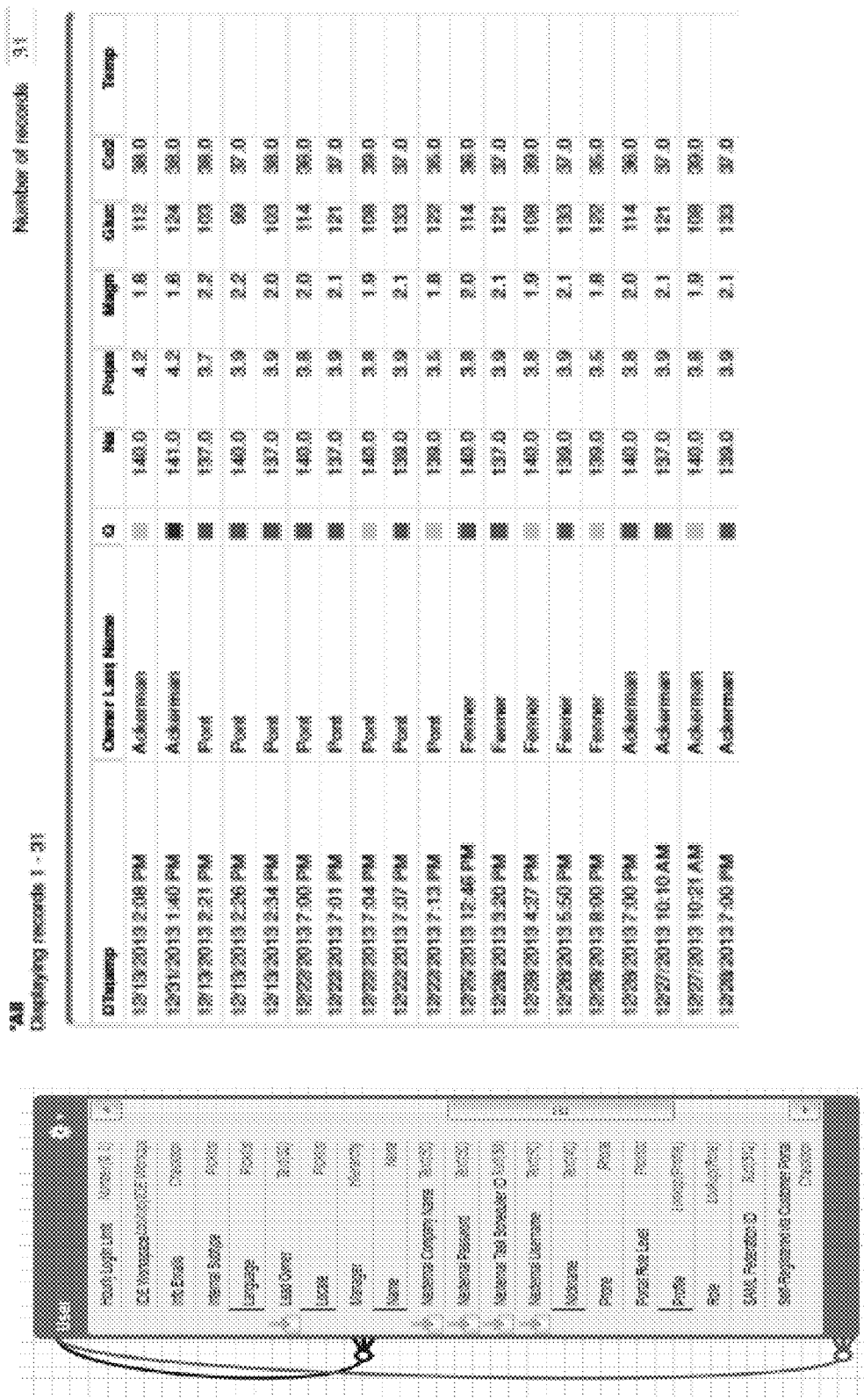
FIG. 27 shows an image of a user data base on the remote computer server.
Figure 30:
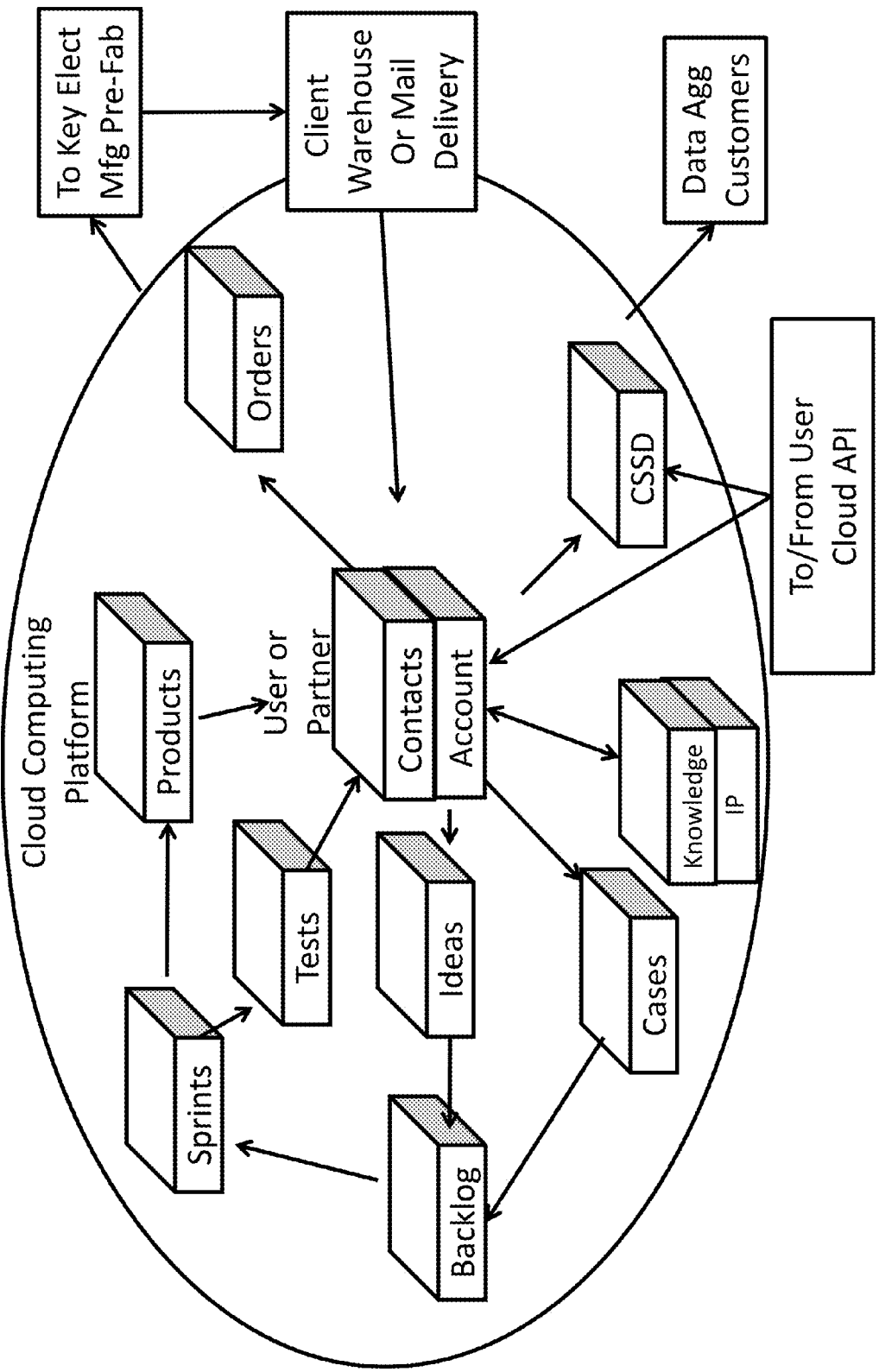
FIG. 30 shows a diagram of another embodiment of a cloud enterprise.

The system architecture is diagrammed in FIG. 20. Here, the remote transceiver device is characterized as a Mobile App, preferably on a smartphone, which is in communication with the sensor apparatus via wireless communication. Mobile App controls and commands are diagrammed in FIG. 21. The Mobile App may network with the user web service, as shown in FIG. 22, to access the cloud database and library, as shown in FIG. 23. An example cloud platform operable with the present invention is the EMITTI platform (ex: Amazon Web Services, Microsoft Azure, or any other similar commercial or private cloud platform); cloud architecture is more specifically detailed in FIG. 28. The web service allows the user to access, analyze, and manipulate user output data that was transmitted from the sensor apparatus. FIG. 24 shows an individual user web front including features such as external sensor correlation, selected session summary, and session tables. FIG. 25 shows the user web front for multiple users. The complete website builder platform is shown in FIG. 26. The website may connect to the cloud computing enterprise, which is diagrammed in FIGS. 29 and 30, or link to social media sites.

Figure 31:
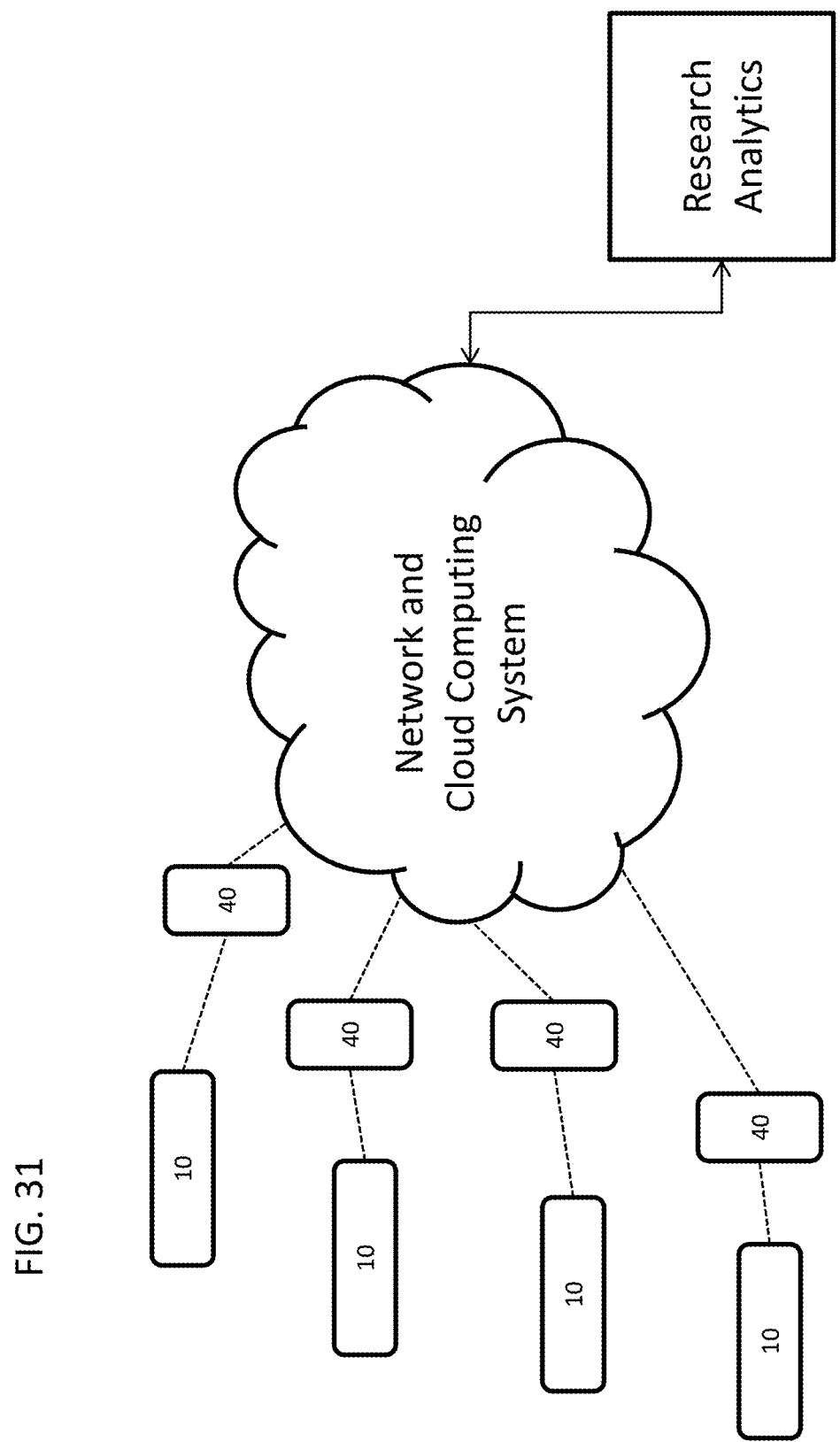
FIG. 31 shows a diagram of a system for epidemiological research.
Figure 32:
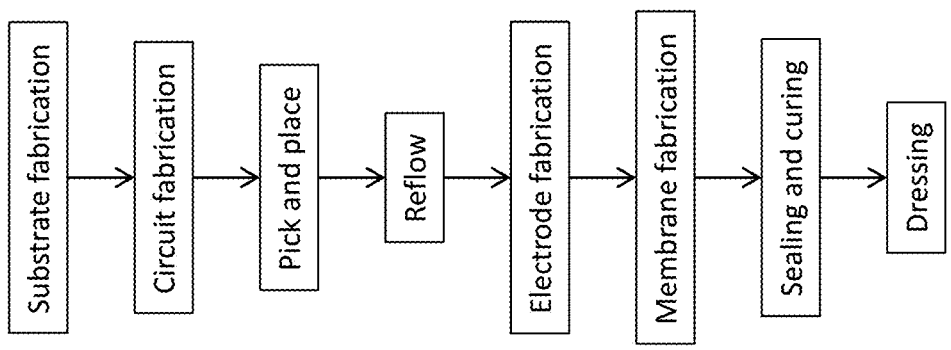
FIG. 32 shows a diagram of a manufacturing process for the sensor apparatus.

From the cloud computing system, data from multiple users may be stored, as diagrammed in FIG. 31. Access to these data may be acquired by researchers and epidemiologists to perform a variety of research analytics. The captured data will preferably be from the same sweat detection model, providing greater reliability to the pool of data. The ability to collect these specific biomarker data from such a large population of subjects creates an invaluable real-time, continuous epidemiological research system and method.

The preferred embodiment of the system includes an apparatus that intimately adheres to mammalian skin. The sweat from the skin is moved into the apparatus for detection of sweat biomarkers and analytes. Where on the mammal the apparatus is positioned is dependent upon, by way of example and not limitation, user preference, sweat collection patterns, or sweat production amounts at a given location.

The apparatus is operable to determine a measured amount of transepidermal sweat and/or a measured amount of evaporative sweat and an estimated amount of transepidermal sweat and/or an estimated amount of evaporative sweat. In one embodiment, estimated amounts are determined based on body surface area, mass, gender, fitness level, weight, and/or age. In another embodiment, the apparatus is operable to compare the estimated amount of transepidermal sweat and/or the estimated amount of evaporative sweat to the measured amount of transepidermal sweat and/or the measured amount of evaporative sweat and provide a status based on the comparison of the estimated amount of transepidermal sweat and/or the estimate amount of evaporative sweat to the measured amount of transepidermal sweat and/or the measured amount of evaporative sweat. In another embodiment, the apparatus uses a tangible/quantifiable fitness level in combination with sweat biomarker ratios in order to calculate real-time sweat rates. In another embodiment, the apparatus uses gender factors in order to improve sweat flow rate accuracy. In another embodiment, the apparatus uses consumption refresh models, exact custom formula to return to start condition.

The apparatus is also operable to model losses and consumption of sweat in order to estimate blood serum characteristics at a time before use, at the start of use, in real-time, or at a time after use. In one embodiment, the apparatus is operable to predict performance erosion and injury probability based on the analysis of at least one biological fluid biomarker. In another embodiment, the apparatus is operable to use the analysis of sweat to provide corrective action recommendations.

Exemplary technologies regarding sensor technology, analysis, communication, and manufacture are illustrated by the following: PCT patent application publication no. PCT/US2013/035092 for sweat stimulation, collection and sensing systems by Heikenfeld, et al. filed Apr. 3, 2013; PCT patent application publication no. PCT/US2014/061083 for devices for integrated, repeated, prolonged, and/or reliable sweat stimulation and biosensing by Heikenfeld and Sonner filed Oct. 17, 2014; PCT patent application publication no. PCT/US2014/061098 for sweat sensing with chronological assurance by Heikenfeld filed Oct. 17, 2014; U.S. provisional patent application Ser. No. 62/003,675 for advanced sweat sensor adhesion, hermetic, and fluidic strategies by Heikenfeld filed May 28, 2014; U.S. provisional patent application Ser. No. 62/003,692 for dermal transport and biomarker sensing devices with preferential targeting of sweat ducts by Heikenfeld filed May 28, 2014; U.S. provisional patent application Ser. No. 62/003,707 for device construction and methods for prolonged and reliable stimulation and sensing by Heikenfeld filed May 28, 2014; U.S. provisional patent application Ser. No. 62/003,715 for vertical flow porous electrode membrane devices for sensing by Heikenfeld and Sonner filed May 28, 2014; U.S. provisional patent application Ser. No. 62/003,233 for combinatorial sensing of sweat biomarkers using simple potentiometry and impedance measurements by Heikenfeld, et al. filed Jul. 11, 2014; U.S. provisional patent application Ser. No. 62/053,388 for sweat sensing with analytical assurance by Heikenfeld filed Sep. 22, 2014; U.S. provisional patent application Ser. No. 62/064,009 for patch communication security and compliance by Heikenfeld, et al. filed Oct. 15, 2014; U.S. provisional patent application Ser. No. 62/074,295 for advanced adhesives for chronological sweat sensors by Heikenfeld filed Nov. 3, 2014; and U.S. provisional patent application Ser. No. 62/114,835 for devices with reduced sweat volumes between sensors and sweat glands by Heikenfeld filed Feb. 11, 2015; each of which is incorporated herein by reference in its entirety.

Figure 33:
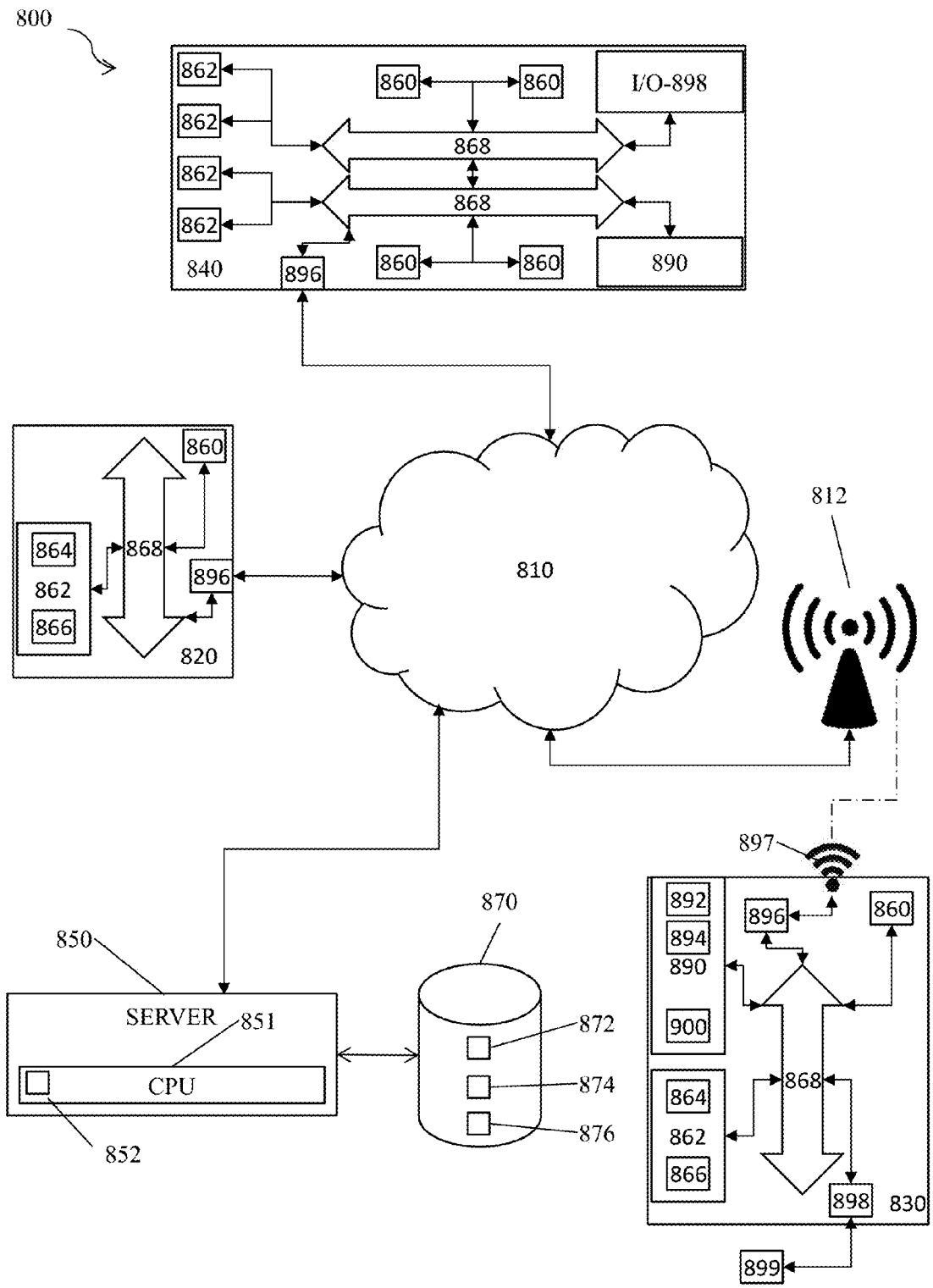
FIG. 33 shows a schematic diagram illustrating general components of a cloud-based computer system.

FIG. 33 is a schematic diagram of an embodiment of the invention illustrating a computer system, generally described as 800, having a network 810, a plurality of computing devices 820, 830, 840, a server 850 and a database 870.

The server 850 is constructed, configured and coupled to enable communication over a network 810 with a computing devices 820, 830, 840. The server 850 includes a processing unit 851 with an operating system 852. The operating system 852 enables the server 850 to communicate through network 810 with the remote, distributed user devices. Database 870 may house an operating system 872, memory 874, and programs 876.

In one embodiment of the invention, the system 800 includes a cloud-based network 810 for distributed communication via a wireless communication antenna 812 and processing by a plurality of mobile communication computing devices 830. In another embodiment of the invention, the system 800 is a virtualized computing system capable of executing any or all aspects of software and/or application components presented herein on the computing devices 820, 830, 840. In certain aspects, the computer system 800 may be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of digital computers 820, 840, 850 and mobile devices 830, such as a server, blade server, mainframe, mobile phone, a personal digital assistant (PDA), a smart phone, a desktop computer, a netbook computer, a tablet computer, a workstation, a laptop, and other similar computing devices. The components shown here, their connections and relationships, and their functions, are meant to be exemplary only, and are not meant to limit implementations of the invention described and/or claimed in this document In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 may additionally include components such as a storage device 890 for storing the operating system 892 and one or more application programs 894, a network interface unit 896, and/or an input/output controller 898. Each of the components may be coupled to each other through at least one bus 868. The input/output controller 898 may receive and process input from, or provide output to, a number of other devices 899, including, but not limited to, alphanumeric input devices, mice, electronic styluses, display units, touch screens, signal generation devices (e.g., speakers) or printers.

By way of example, and not limitation, the processor 860 may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 33, multiple processors 860 and/or multiple buses 868 may be used, as appropriate, along with multiple memories 862 of multiple types (e.g., a combination of a DSP and a microprocessor, a plurality of microprocessors, one or more microprocessors in conjunction with a DSP core).

Also, multiple computing devices may be connected, with each device providing portions of the necessary operations (e.g., a server bank, a group of blade servers, or a multi-processor system). Alternatively, some steps or methods may be performed by circuitry that is specific to a given function.

According to various embodiments, the computer system 800 may operate in a networked environment using logical connections to local and/or remote computing devices 820, 830, 840, 850 through a network 810. A computing device 830 may connect to a network 810 through a network interface unit 896 connected to the bus 868. Computing devices may communicate communication media through wired networks, direct-wired connections or wirelessly such as acoustic, RF or infrared through an antenna 897 in communication with the network antenna 812 and the network interface unit 896, which may include digital signal processing circuitry when necessary. The network interface unit 896 may provide for communications under various modes or protocols.

In one or more exemplary aspects, the instructions may be implemented in hardware, software, firmware, or any combinations thereof. A computer readable medium may provide volatile or non-volatile storage for one or more sets of instructions, such as operating systems, data structures, program modules, applications or other data embodying any one or more of the methodologies or functions described herein. The computer readable medium may include the memory 862, the processor 860, and/or the storage media 890 and may be a single medium or multiple media (e.g., a centralized or distributed computer system) that store the one or more sets of instructions 900. Non-transitory computer readable media includes all computer readable media, with the sole exception being a transitory, propagating signal per se. The instructions 900 may further be transmitted or received over the network 810 via the network interface unit 896 as communication media, which may include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and nonvolatile media such as cache, RAM, ROM, EPROM, EEPROM, FLASH memory or other solid state memory technology, disks or discs (e.g., digital versatile discs (DVD), HD-DVD, BLURAY, compact disc (CD), CD-ROM, floppy disk) or other optical storage, magnetic cassettes, magnetic tape, magnetic disk storage or other magnetic storage devices, or any other medium that can be used to store the computer readable instructions and which can be accessed by the computer system 800.

It is also contemplated that the computer system 800 may not include all of the components shown in FIG. 33, may include other components that are not explicitly shown in FIG. 33, or may utilize an architecture completely different than that shown in FIG. 33. The various illustrative logical blocks, modules, elements, circuits, and algorithms described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

By way of definition and description supporting the claimed subject matter, preferably, the present invention includes communication methodologies for transmitting data, data packets, messages or messaging via a communication layer. Wireless communications over a network are preferred. Correspondingly, and consistent with the communication methodologies for transmitting data or messaging according to the present invention, as used throughout this specification, figures and claims, wireless communication is provided by any reasonable protocol or approach, by way of example and not limitation, Bluetooth, Wi-Fi, cellular, zigbee, near field communication, or other similar commercially utilized standards; the term "ZigBee" refers to any wireless communication protocol adopted by the Institute of Electronics & Electrical Engineers (IEEE) according to standard 802.15.4 or any successor standard(s), the term "Wi-Fi" refers to any communication protocol adopted by the IEEE under standard 802.11 or any successor standard(s), the term "WiMax" refers to any communication protocol adopted by the IEEE under standard 802.16 or any successor standard(s), and the term "Bluetooth" refers to any short-range communication protocol implementing IEEE standard 802.15.1 or any successor standard(s). Additionally or alternatively to WiMax, other communications protocols may be used, including but not limited to a "1G" wireless protocol such as analog wireless transmission, first generation standards based (IEEE, ITU or other recognized world communications standard), a "2G" standards based protocol such as "EDGE or CDMA 2000 also known as 1×RTT", a 3G based standard such as "High Speed Packet Access (HSPA) or Evolution for Data Only (EVDO), any accepted 4G standard such as "IEEE, ITU standards that include WiMax, Long Term Evolution "LTE" and its derivative standards, any Ethernet solution wireless or wired, or any proprietary wireless or power line carrier standards that communicate to a client device or any controllable device that sends and receives an IP based message. The term "High Speed Packet Data Access (HSPA)" refers to any communication protocol adopted by the International Telecommunication Union (ITU) or another mobile telecommunications standards body referring to the evolution of the Global System for Mobile Communications (GSM) standard beyond its third generation Universal Mobile Telecommunications System (UMTS) protocols. The term "Long Term Evolution (LTE)" refers to any communication protocol adopted by the ITU or another mobile telecommunications standards body referring to the evolution of GSM-based networks to voice, video and data standards anticipated to be replacement protocols for HSPA. The term "Code Division Multiple Access (CDMA) Evolution Date-Optimized (EVDO) Revision A (CDMA EVDO Rev. A)" refers to the communication protocol adopted by the ITU under standard number TIA-856 Rev. A.

It will be appreciated that embodiments of the invention described herein may be comprised of one or more conventional processors and unique stored program instructions that control the one or more processors to implement, in conjunction with certain non-processor circuits, some, most, or all of the functions for the systems and methods as described herein. The non-processor circuits may include, but are not limited to, radio receivers, radio transmitters, antennas, modems, signal drivers, clock circuits, power source circuits, relays, current sensors, and user input devices. As such, these functions may be interpreted as steps of a method to distribute information and control signals between devices. Alternatively, some or all functions could be implemented by a state machine that has no stored program instructions, or in one or more application specific integrated circuits (ASICs), in which each function or some combinations of functions are implemented as custom logic. Of course, a combination of the two approaches could be used. Thus, methods and means for these functions have been described herein. Further, it is expected that one of ordinary skill in the art, notwithstanding possibly significant effort and many design choices motivated by, for example, available time, current technology, and economic considerations, when guided by the concepts and principles disclosed herein, will be readily capable of generating such software instructions, programs and integrated circuits (ICs), and appropriately arranging and functionally integrating such non-processor circuits, without undue experimentation.

Certain modifications and improvements will occur to those skilled in the art upon a reading of the foregoing description, by way of example, a device having at least one microprocessor for storing data may be operable in the device before data transmission. Another example includes other advanced sensors, as well as being incorporated into smart fabrics and protective wear. Advanced sensors include advanced sweat biomarkers, pulse rate breath rate, micro EKG, micro O2, picture log, voice log, voice translate, tissue safe X-ray and combinations thereof. Smart fabrics incorporate the present invention and include active heat/cooling, kinetic energy generation, electromagnetic energy harvesting, wearable energy storage, wearable data storage, wearable processing, wearable communications, elastomeric actuators, and combinations thereof. More generally, the apparatus may be part of apparel and material for clothing, wherein the clothing may be for lower body, like socks and athletic underwear, upper body, like shirts and forearm bands, or head, like stocking cap or headband. The present invention is also incorporated into enhanced protective wear such as enhanced helmets, gloves and footwear. Enhanced helmets include those with MRI, 3D audio, visual enhancement, mixed reality, breath sensors, aerosol nutrition and combinations thereof. Enhanced gloves include touch communications, elastomeric grip, gesture control and combinations thereof. Enhanced footwear includes power generation boots, 3D tracking, tactile alerts, communication transceivers, and combinations thereof.

The above mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the present invention.

What is claimed is:

1. A cloud-based system for analyzing sweat from a human and transmitting and storing sweat data from the human comprising:
    an apparatus for sensing and analyzing sweat, wherein the apparatus includes an electronic layer comprising at least one electrochemical sensor, a microcontroller, and a transceiver antenna coil;
    at least one remote transceiver device; and
    at least one remote computer server;
    wherein the apparatus analyzes at least one sweat biomarker, calculates at least one output datum of the at least one sweat biomarker using at least one algorithm, and transmits the at least one output datum to the at least one remote transceiver device;
    wherein the at least one algorithm calculates the at least one output datum using an estimated body surface area of a human and input data, wherein the input data includes at least a height and a weight of the human, and wherein the height and the weight of the human are used to estimate the estimated body surface area of the human;
    wherein the at least one remote transceiver device transmits the at least one output datum to the at least one remote computer server for storage in a cloud database and/or processing;
    wherein the apparatus and the at least one remote transceiver device have real-time or near-real-time two-way communication; and
    wherein the apparatus is flexible and further includes:
        a macrofluidic, double-sided adhesive layer;
        a microfluidic management layer; and
        a vapor porous, top protective layer;
    wherein the macrofluidic, double-sided adhesive layer is intimately adhered to an exterior layer of human skin;
    wherein the microfluidic management layer is positioned between the macrofluidic, double-sided adhesive layer and the electronic layer;
    wherein the microfluidic management layer circumferentially surrounds the at least one electrochemical sensor of the electronic layer;
    wherein the at least one electrochemical sensor of the electronic layer is facing the exterior layer of human skin;
    wherein the electronic layer is intimately adhered to the macrofluidic, double-sided adhesive layer;
    wherein the vapor porous, top protective layer is placed on and completely covers the microfluidic management layer and the electronic layer; and
    wherein the vapor porous, top protective layer is intimately adhered to the macrofluidic, double-sided adhesive layer.

2. The system of claim 1, wherein the at least one sweat biomarker includes small molecules, proteins, metabolites, and/or electrolytes.

3. The system of claim 1, wherein the microcontroller receiver multiple input data, which are input from multiple sources including the sweat.

4. The system of claim 1, wherein the at least one electrochemical sensor houses at least one standard electrode and at least one active electrode.

5. The system of claim 4, wherein the at least one standard and/or the at least one active electrode are silver, zinc, copper, gold, platinum, rhodium, carbon, or a combination thereof.

6. The system of claim 1, wherein the apparatus wirelessly transmits the at least one output datum to the at least one remote transceiver device.

7. The system of claim 6, wherein the apparatus wirelessly transmits the at least one output datum via Bluetooth, radiofrequency, zigbee, wi-fi, or near field communication.

8. The system of claim 1, wherein the apparatus continuously monitors the at least one sweat biomarker.

9. The system of claim 1, wherein the input data further includes gender, fitness or conditioning level, age, and a maximum rate of oxygen consumption for the human (VO2 max).

10. The system of claim 1, wherein the two-way communication further comprises commands, electrode calibration, microcontroller software updates, new or updated algorithms, new or updated modifying variables for algorithms, microcontroller health properties, error codes, electrode maintenance or malfunction, or a combination thereof.

11. The system of claim 1, wherein the at least one remote computer server includes a library and wherein the library is operable to perform file storage, security, extensions, utilities, scheduling, messaging, persistence, cache, and logging functions.

12. The system of claim 1, wherein the at least one remote computer server automatically validates data.

13. The system of claim 1, wherein the at least one remote computer server triggers a series of workflows based on the type, date/time stamps, and scope of data to correlate and identify trends.

14. The system of claim 1, further including a mobile application on the at least one remote transceiver device.

15. A cloud-based method for analyzing sweat from a human and transmitting and storing sweat data from the human, the method comprising:
    providing an apparatus for sensing and analyzing sweat, wherein the apparatus includes an electronic layer comprising at least one electrochemical sensor, a microcontroller, and a transceiver antenna coil; at least one remote transceiver device;
    and at least one remote computer server;
    wherein the at least one remote transceiver device and the apparatus are operable for two-way cross-communication in real-time or near-real-time;
        the at least one electrochemical sensor sensing at least one biomarker of the sweat, which creates a voltage;
        the microcontroller converting the at least one biomarker of the sweat into at least one output datum using at least one algorithm, wherein the at least one algorithm calculates the at least one output datum using an estimated body surface area of a human and input data, wherein the input data includes at least a height and a weight of the human, and wherein the height and the weight of the human are used to estimate the estimated body surface area of the human;

the at least one remote transceiver device inputting modifying variables into the at least one algorithm via the two-way communication with the apparatus;

the transceiver antenna coil transmitting the at least one output datum to the at least one remote transceiver device via the two-way communication with the apparatus;

the at least one remote transceiver device sharing or transmitting the at least one datum with the at least one remote computer server for storage in a cloud database and/or processing; and wherein the apparatus is flexible and further includes:
a macrofluidic, double-sided adhesive layer;
a microfluidic management layer; and
a vapor porous, top protective layer;

wherein the macrofluidic, double-sided adhesive layer is intimately adhered to an exterior layer of human skin;

wherein the microfluidic management layer is positioned between the macrofluidic, double-sided adhesive layer and the electronic layer;

wherein the microfluidic management layer circumferentially surrounds the at least one electrochemical sensor of the electronic layer;

wherein the at least one electrochemical sensor of the electronic layer is facing the exterior layer of human skin;

wherein the electronic layer is intimately adhered to the macrofluidic, double-sided adhesive layer;

wherein the vapor porous, top protective layer is placed on and completely covers the microfluidic management layer and the electronic layer; and wherein the vapor porous, top protective layer is intimately adhered to the macrofluidic, double-sided adhesive layer.

16. The method of claim 15, wherein the at least one biomarker of the sweat includes small molecules, proteins, metabolites, and/or electrolytes.

17. The method of claim 15, wherein the at least one output datum includes but is not limited to concentrations, such as molarity, osmolarity, and osmolality, and/or descriptive statistics, such as averages, ratios, and trends, all of which may be categorized based on a sub-range within a larger physiological range of the at least one biomarker.

18. The method of claim 15, wherein the at least one output datum is transmitted from the apparatus to a remote computer device through wireless network communication by the transceiver antenna of the apparatus.

19. The method of claim 18, wherein the wireless network communication is via Bluetooth, radiofrequency, zigbee, wi-fi, or near field communication.

20. A cloud-based system for continuously analyzing sweat from a human in real-time and transmitting and storing sweat data from the human comprising:
an apparatus for sensing and analyzing sweat, wherein the apparatus includes an electronic layer comprising at least one electrochemical sensor, a microcontroller, and a transceiver antenna coil;
at least one remote transceiver device; and
at least one remote computer server;

wherein the apparatus continuously analyzes at least one sweat biomarker in real-time, calculates at least one output datum of the at least one sweat biomarker using at least one algorithm, and transmits the at least one output datum to the at least one remote transceiver device;

wherein the at least one algorithm calculates the at least one output datum using an estimated body surface area of a human and input data, wherein the input data includes at least a height and a weight of the human, a maximum rate of oxygen consumption for the human ($VO_2$ max), and a body mass of the human, and wherein the height and the weight of the human are used to estimate the estimated body surface area of the human;

wherein the at least one remote transceiver device transmits the at least one output datum to the at least one remote computer server for storage in a cloud database and/or processing;

wherein the apparatus and the at least one remote transceiver device have real-time or near-real-time two-way communication;

wherein the electrochemical sensor has at least one reference electrode and at least one active electrode;

wherein the at least one active electrode has an ionophore polymer coating;

wherein the apparatus is flexible and further includes:
a macrofluidic, double-sided adhesive layer;
a microfluidic management layer; and
a vapor porous, top protective layer;

wherein the macrofluidic, double-sided adhesive layer is intimately adhered to an exterior layer of human skin;

wherein the microfluidic management layer is positioned between the macrofluidic, double-sided adhesive layer and the electronic layer;

wherein the microfluidic management layer circumferentially surrounds the at least one electrochemical sensor of the electronic layer;

wherein the at least one electrochemical sensor of the electronic layer is facing the exterior layer of human skin;

wherein the electronic layer is intimately adhered to the macrofluidic, double-sided adhesive layer;

wherein the vapor porous, top protective layer is placed on and completely covers the microfluidic management layer and the electronic layer; and wherein the vapor porous, top protective layer is intimately adhered to the macrofluidic, double-sided adhesive layer.

* * * * *